US009662283B2

United States Patent
Lemoine et al.

(10) Patent No.: US 9,662,283 B2
(45) Date of Patent: *May 30, 2017

(54) COLOUR CHANGING COMPOSITION

(71) Applicant: L'OREAL, Paris (FR)

(72) Inventors: Cyril Lemoine, Shanghai (CN); XueDong Liu, Shanghai (CN); Juan Chu, Shanghai (CN); Qing Yu, Shanghai (CN)

(73) Assignee: L'OREAL, Paris (FR)

( * ) Notice: Subject to any disclaimer, the term of this patent is extended or adjusted under 35 U.S.C. 154(b) by 195 days.

This patent is subject to a terminal disclaimer.

(21) Appl. No.: 14/372,862

(22) PCT Filed: Jan. 16, 2013

(86) PCT No.: PCT/CN2013/070564
§ 371 (c)(1),
(2) Date: Jul. 17, 2014

(87) PCT Pub. No.: WO2013/107350
PCT Pub. Date: Jul. 25, 2013

(65) Prior Publication Data
US 2014/0356402 A1 Dec. 4, 2014

(30) Foreign Application Priority Data

Jan. 17, 2012 (WO) ................ PCT/CN2012/070486

(51) Int. Cl.
A61K 8/11 (2006.01)
A61Q 1/04 (2006.01)
(Continued)

(52) U.S. Cl.
CPC ................ A61K 8/11 (2013.01); A61K 8/345 (2013.01); A61K 8/553 (2013.01); A61K 8/60 (2013.01);
(Continued)

(58) Field of Classification Search
None
See application file for complete search history.

(56) References Cited

U.S. PATENT DOCUMENTS 4,756,906 A 7/1988 Sweeny
4,879,174 A 11/1989 Marabella
(Continued)

FOREIGN PATENT DOCUMENTS

CH EP 2277982 A1 * 1/2011 ............... A61K 8/11
CN 102088946 A 6/2011
(Continued)

OTHER PUBLICATIONS

U.S. Appl. No. 14/372,872, filed Jul. 17, 2014, Zhu, et al.
(Continued)

*Primary Examiner* — Isaac Shomer
(74) *Attorney, Agent, or Firm* — Oblon, McClelland, Maier & Neustadt, L.L.P.

(57) ABSTRACT

A changing color composition for caring for and/or making up keratin materials is disclosed. The composition comprises in a physiologically acceptable medium, at least: a) microcapsules containing releasable colorant(s), said microcapsules comprising: a core comprising one organic material, at least one layered coating surrounding said core, the layered coating comprising at least one polymer, at least one colorant, and advantageously at least one lipid-based material, b) at least 3% by weight, preferably at least 5 by weight, more preferably at least 8% by weight and advantageously at least 10% by weight relative to the weight of the composition of an aqueous phase comprising water and at least one compound chosen from polyols, glycols and $C_2$-$C_8$ monoalcohols, and mixtures thereof, c) at least one hydrophilic gelifying agent, d) and optionally 0.1 to 70% by weight relative to the weight of the composition, of additional cosmetic ingredient(s) selected from volatile and (Continued)

non-volatile silicon or hydrocarbon oils, surfactants, filler, thickening agents, film forming agents, polymers, preservatives, silicon elastomer, self-tanning agents, additional non-entrapped colorants, cosmetic actives, pH regulators, perfumes, and mixtures thereof.

13 Claims, 5 Drawing Sheets

(51) Int. Cl.
   *A61K 8/34* (2006.01)
   *A61Q 1/06* (2006.01)
   *A61K 8/55* (2006.01)
   *A61K 8/60* (2006.01)
   *A61K 8/73* (2006.01)
   *A61Q 1/02* (2006.01)

(52) U.S. Cl.
   CPC ............... *A61K 8/73* (2013.01); *A61Q 1/02* (2013.01); *A61Q 1/04* (2013.01); *A61Q 1/06* (2013.01); *A61K 2008/115* (2013.01); *A61K 2800/412* (2013.01); *A61K 2800/42* (2013.01)

(56) References Cited

U.S. PATENT DOCUMENTS

| | | | |
|---|---|---|---|
| 5,411,802 | A | 5/1995 | Kumar et al. |
| 5,861,440 | A | 1/1999 | Gohla et al. |
| 2007/0220686 | A1 | 9/2007 | Jeanne-Rose et al. |
| 2007/0231055 | A1 | 10/2007 | Albisetti |
| 2008/0292692 | A1 | 11/2008 | Pilch et al. |
| 2011/0229536 | A1* | 9/2011 | Kvitnitsky ........... A61K 8/0212 424/401 |
| 2012/0178662 | A1 | 7/2012 | Lachmann et al. |
| 2012/0183479 | A1 | 7/2012 | Loeffler et al. |

FOREIGN PATENT DOCUMENTS

| | | |
|---|---|---|
| EP | 0 232 001 A2 | 8/1987 |
| EP | 1 776 985 A2 | 4/2007 |
| EP | 1 776 985 A3 | 4/2007 |
| EP | 2 277 982 A1 | 1/2011 |
| FR | 2 591 102 A1 | 6/1987 |
| FR | 2 848 879 A1 | 6/2004 |
| JP | 62-252715 A | 11/1987 |
| JP | 04-001118 A | 1/1992 |
| JP | 07-258033 A | 10/1995 |
| JP | 08-175932 A | 7/1996 |
| JP | 09-100469 A | 4/1997 |
| JP | 2010-235563 A | 10/2010 |
| JP | 2011-079804 A | 4/2011 |
| WO | WO 94/23688 A2 | 10/1994 |
| WO | WO 95/11747 A1 | 5/1995 |
| WO | WO 01/35933 A2 | 5/2001 |
| WO | WO 01/35933 A3 | 5/2001 |
| WO | WO 2008/147619 A1 | 12/2008 |
| WO | WO 2009/138978 A2 | 11/2009 |
| WO | WO 2010/097558 A2 | 9/2010 |
| WO | WO 2011/006657 A1 | 1/2011 |

OTHER PUBLICATIONS

U.S. Appl. No. 14/372,888, filed Jul. 17, 2014, Chai, et al.
International Search Report and Written Opinion issued Apr. 25, 2013 in PCT/CN2013/070564.
International Search Report and Written Opinion issued Oct. 25, 2012 in PCT/CN2012/070486.
International Search Report and Written Opinion issued Apr. 25, 2013 in PCT/CN2013/070569.
International Search Report and Written Opinion issued Nov. 1, 2012 in PCT/CN2012/070483.
International Search Report and Written Opinion issued Apr. 25, 2013 in PCT/CN2013/070559.
International Search Report and Written Opinion issued Nov. 8, 2012 in PCT/CN2012/070490.
International Search Report and Written Opinion issued Apr. 25, 2013 in PCT/CN2013/070566.
International Search Report and Written Opinion issued Oct. 25, 2012 in PCT/CN2012/070497.
International Search Report and Written Opinion issued Apr. 23, 2013 in PCT/JP2013/051227.
International Search Report and Written Opinion issued Jun. 5, 2012 in PCT/JP2012/051476.
U.S. Appl. No. 14/443,722, filed May 19, 2015, Liu, et al.

* cited by examiner

COLOUR CHANGING COMPOSITION

CROSS REFERENCE TO RELATED APPLICATIONS

The present application is a 35 U.S.C. §371 national stage patent application of International patent application PCT/CN2013/070564, filed on Jan. 16, 2013, published as WO/2013/107350 on Jul. 25, 2013, the text of which is incorporated by reference, and claims the benefit of the filing date of application no. PCT/CN2012/070486, filed on Jan. 17, 2012, the text of which is also incorporated by reference.

TECHNICAL FIELD

The present invention relates to a color-changing composition in particular useful for care, hygiene and/or makeup of keratin materials.

In particular, a color-changing composition according to the invention may be any type of cosmetic composition such as a foundation, a face powder, an eye shadow, a concealer product, a blusher, a lipstick, a lip balm, a lip gloss, a lip pencil, an eye pencil, an eyeliner, a mascara, a body makeup product, a skin colouring product, a care product such as a care cream, a 'BB' product (Blemish Balm product able to cover imperfections), a tinted cream or an antisun product, preferably a foundation or 'BB' product. The color-changing composition according to the invention may be liquid, solid or a powder.

A composition of the invention is especially a composition intended to be applied to a keratin material, in particular the skin and more particularly facial skin, such as a skin care or make-up product for face.

According to another embodiment, the composition of the invention is a mascara.

According to another embodiment, the composition of the invention is a product for lips, in particular a lipgloss, a lipbalm or a lipstick.

BACKGROUND ART

Cosmetic compositions, especially foundations, are commonly used to give the skin an aesthetic colour, but also to hide skin imperfections such as redness and/or marks. In this regard, many formulations have been developed to date.

In this respect, there is a growing interest in cosmetic products that provide a change in color in response to external incentives such for example shear force.

Generally, this purpose is achieved by including in cosmetic composition microencapsulated colorants wherein, upon application on the skin, the composition provides the expected changing color. More particularly, the change of color is provided by the colorant-containing microcapsules, which upon rupture by application of a mechanical force, release the entrapped colorant into the composition, thereby changing its color. A mechanical action such as rubbing spread the topical composition and facilitates its penetration into the skin. The immediate change of color of the composition provides a visual esthetical effect.

Different types of entrapped colorants and more particularly pigments-containing microcapsules are already available. They mainly differ through the type of entrapping material(s) and/or the type of encapsulation.

Thus, as pigments encapsulated by microcapsules in acrylic acid and/or methacrylic acid polymers or copolymers, it may be cited for example microcapsules containing copolymer of ethyl acrylate/methacrylic acid ammonium salts, commercialized by the Tagra company and described in WO-A-01/35933. It may be also cited the encapsulated pigments commercialized by TAGRA BIOTECHNOLOGIES under the name BLACKCAP1©, YELLOWCAP1©, REDCAP1©, BLACKCAP3©, YELLOWCAP3©, REDCAP3©.

As pigments encapsulated by microspheres in cellulose derivatives, it can be cited for example spheres comprising cellulose, hydroxypropyl methylcellulose, commercialized by the Induchem company under the name Unisphere©.

As pigments encapsulated by microcapsules in polymers of polyester, polyaminomethacrylate, polyvinylpyrrolidone, hydroxypropylmethylcellulose, shellac types and mixtures thereof, it may be notably cited those described in the application US 2011/0165208 of Biogenics and commercialized under the name Magicolor© by Biogenics.

As other pigments encapsulated by microcapsules may also be cited the ones disclosed by DAITO in JP2011-79804 may be also cited the pigment-encapsulated double-layer microcapsules comprising three or more of the following (a) mannitol, (b) hydrogenated lecithin, (c) polymethylmethacrylate, (d) cellulose and (e) shellac.

These double-layer microcapsules do not comprise an uncoloured core as the one of the microcapsules preferably used according to the invention, but rather a colored inner layer containing the aforesaid components which are mixed all together and then granulated.

However, with some colorant-containing microcapsules it may be difficult to permanently retain the colorant over long periods of time and when subjected to different environments and conditions. This is true of pigments, oil soluble dyes, and water soluble dyes. Thus, some microcapsules described in patents and publications have been found to gradually release the colorant, or to "bleed", over time when tested for prolonged periods at elevated temperatures. Color bleed occurs when a dye or pigment migrates through or off of microspheres/microcapsules through contact with moisture and/or other ingredients in a formulation such as alcohols or glycols, surfactants, silicones, oils, preservatives, salts and other components typically found in cosmetic formulations. Leeching or bleed of the colorant in cosmetic composition can impair the long term visual effect of the cosmetic both in the container and on the substrate.

Furthermore, some pigment-containing microcapsules may confer a lower coverage effect than expected.

Furthermore, some pigment-containing microcapsules are immediately broken down at the time of application so, while there is the fun of a sudden colour change, it has not been possible to realise intermediate stages in this colour change or to adjust the colour gradation.

Furthermore, some pigment-containing microcapsules may have some stability issues depending on the cosmetic composition and with associated solvents/ingredients.

Furthermore, some pigment-containing microcapsules may have a grey color aspect that confers a not attractive color in the bulk of the cosmetic composition.

At last, some microcapsules may provide a discomfort and/or unfavourable feeling when the cosmetic formulation including them is applied on a keratin material.

SUMMARY OF INVENTION

Thus there is a need to provide cosmetic composition with colorant-containing microcapsules having improved color bleed resistance. In this respect, there is a need of colorant-containing microcapsules, which capsules retain good shatter resistance and exhibit improved bleed resistance. In a cosmetic composition if the dye is not permanently retained, this can impair the long-term visual effect of the cosmetic.

There is also a need to provide a cosmetic composition which allows the preferred colouration or gradation pattern to be adjusted by varying the method or intensity of application onto the skin or the use of microcapsules containing different colorants.

There is also a need to provide a cosmetic composition stable with a large panel of solvent/ingredient associated.

There is also a need to provide a cosmetic composition wherein the microcapsules are or are not visible inside the bulk of the composition depending on the desired appearance.

There is also a need for a cosmetic composition containing pigment-encapsulated microcapsules which do not provoke to the user a discomfort feeling when applied.

There is also a need to provide a cosmetic composition containing pigment-encapsulated microcapsules which disintegrate rapidly indeed immediately when applied, with a liquid feeling on the skin and leading to coloured compositions devoid of any granular aspect. Particularly, the composition may present different shades or color gradations depending on the rubbing strength.

There is also a need to provide pigment-encapsulated microcapsules with a hardness sufficient to be compounded in an industrial process without alteration. Advantageously the hardness of the microcapsules does not significantly decrease during the preparation process.

Surprisingly and advantageously, the compositions according to the invention meet the needs of the prior art.

Thus, according to one of its aspects, a subject of the invention is a changing colour composition for caring for and/or making up keratin materials comprising, in a physiologically acceptable medium, at least:

a) microcapsules containing releasable colorant(s), said microcapsules comprising:
  a core comprising one organic material,
  at least one layered coating surrounding said core, the layered coating comprising
  at least one polymer,
  at least one colorant,
  and advantageously at least one lipid-based material, b) at least 3% by weight, preferably at least 5% by weight, more preferably at least 8% by weight and advantageously at least 10% by weight relative to the weight of the composition of an aqueous phase comprising water and at least one compound chosen from polyols, glycols, $C_2$-$C_8$ monoalcohols, and mixtures thereof, c) at least one hydrophilic gelifying agent, d) and optionally 0.1 to 70% by weight relative to the weight of the composition, of additional cosmetic ingredient(s) selected from volatile and non-volatile silicon or hydrocarbon oils, surfactants, fillers, thickening agents, film forming agents, polymers, preservatives, silicone elastomer, self-tanning agents, additional non-entrapped colorants, cosmetic actives, pH regulators, perfumes, and mixtures thereof.

Preferably, the microcapsules comprise at least two layers, preferably at least one organic inner layer and one organic outer layer of different colour.

Preferably, the core comprises at least one monosaccharide or its derivatives as said organic material, in particular a monosaccharide-polyol advantageously selected from mannitol, erythritol, xylitol, sorbitol and mixtures thereof, preferably mannitol.

Preferably, the layered coating surrounding said core comprises at least one hydrophilic polymer(s) selected from the group consisting of:
  acrylic or methacrylic acid homopolymers or copolymers or salts and esters thereof;
  copolymers of acrylic acid and of acrylamide and its salts and esters thereof;
  polyhydroxycarboxylic acids and its salts and esters thereof;
  polyacrylic acid/alkyl acrylate copolymers, preferably modified or unmodified carboxyvinyl polymers;
  AMPS;
  AMPS/acrylamide copolymers;
  polyoxyethylenated AMPS/alkyl methacrylate copolymers;
  anionic, cationic, amphoteric or nonionic chitin or chitosan polymers;
  cellulose polymers and derivatives;
  Starch polymers and derivatives, eventually modified;
  vinyl polymers and derivatives;
  polymers of natural origins and derivatives thereof;
  alginates and carrageenans;
  glycoaminoglycans, hyaluronic acid and derivatives thereof;
  mucopolysaccharides such as hyaluronic acid and chondroitin sulfates; and the mixtures thereof.

Advantageously the layered coating comprises at least hydrophilic polymer(s) selected from the group consisting of polysaccharides and derivatives, acrylic or methacrylic acid homopolymers or copolymers or salts and esters thereof, and their mixture; the polysaccharides and derivatives are preferably selected from chitosan polymers, chitin polymers, cellulose polymers, starch polymers, galactomannans, alginates, carrageenans, mucopolysaccharides, and their derivatives, and the mixture thereof, more preferably starch polymers and derivatives, cellulose polymers and derivatives, and their mixture.

Particularly the hydrophilic polymer(s) is selected from the polysaccharides and derivatives including one type of ose or several type of ose(s), preferably several type of ose(s) including at least D-glucose units.

Particularly the hydrophilic polymer is selected from starch or derivatives, celluloses or derivatives, preferably starch or derivatives.

Preferably, the core comprises at least one monosaccharide polyol, preferably selected from mannitol, erythritol, xylitol, sorbitol, and the coating comprises at least one polysaccharides (or its derivatives) including as oses at least D-Glucose unit(s), preferably selected from starch or derivatives, celluloses or derivatives, preferably starch or derivatives.

Preferably, the microcapsules include at least one lipid based material, preferably with amphiphilic properties such as lecithins and in particular hydrogenated lecithin.

Advantageously the core represents from 1% to 50% by weight, preferably 5 to 30% by weight, and in particular from 10 to 20% by weight relative to the total weight of the microcapsule.

Advantageously, the colorant(s) represent from 20% to 90%, preferably from 30% to 80%; in particular from 50% to 75% by weight relative to the microcapsule.

Advantageously, the microcapsules have a size of from 50 µm to 800 µm, in particular from 60 µm to 600 µm, and in particular from 80 µm to 500 µm, and in particular from 100 µm to 400 µm.

Preferably the microcapsules containing releasable colorant(s) are multi-layered microcapsules containing releasable colorant(s), said microcapsules comprising:

an uncoloured core consisting in one organic material, and a multi-layered coating surrounding said core and comprising at least one organic inner layer and one organic outer layer of different colour and entrapping respectively at least one colorant.

According to an embodiment, each layer from the microcapsule contains at least one specific colorant or a specific blend of colorant(s).

According to another embodiment, the outer layer from the microcapsule contains at least one specific colorant or a specific blend of colorant(s).

Particularly the colorants are pigments, preferably selected from the group consisting of metallic oxides.

According to an embodiment, one layer from the microcapsule only contains titanium dioxide ($TiO_2$) as colorant.

Particularly the microcapsules comprises at least:

a inner core made of monosaccharide-polyol, preferably mannitol, at least two layers of different colour, at least one hydrophilic polymer preferably selected from polysaccharide or derivatives, and more preferably from starch or derivatives, and advantageously at least one lipid based material, preferably an amphiphilic compound, more preferably a phospholipid, even more preferably phosphoacylglycerol such as hydrogenated lecithin.

The composition may comprise at least 0.1% to 20% by weight, preferably between 0.5% and 15% by weight and in particular between 2 and 10% by weight of microcapsules based on weight of the composition.

Advantageously the microcapsules are deformable in the presence of the said aqueous phase comprising water and at least one compound chosen from polyols, glycols and $C_2$-$C_8$ monoalcohols, and mixtures thereof.

Advantageously the microcapsules inside the composition are breakable under pressure at the application on the keratinic materials.

The present invention is also directed to a process for caring for and/or making up keratinic materials, comprising application on said keratinic materials in particular on the skin of a composition according to the invention.

DESCRIPTION OF EMBODIMENTS

Figure 1:
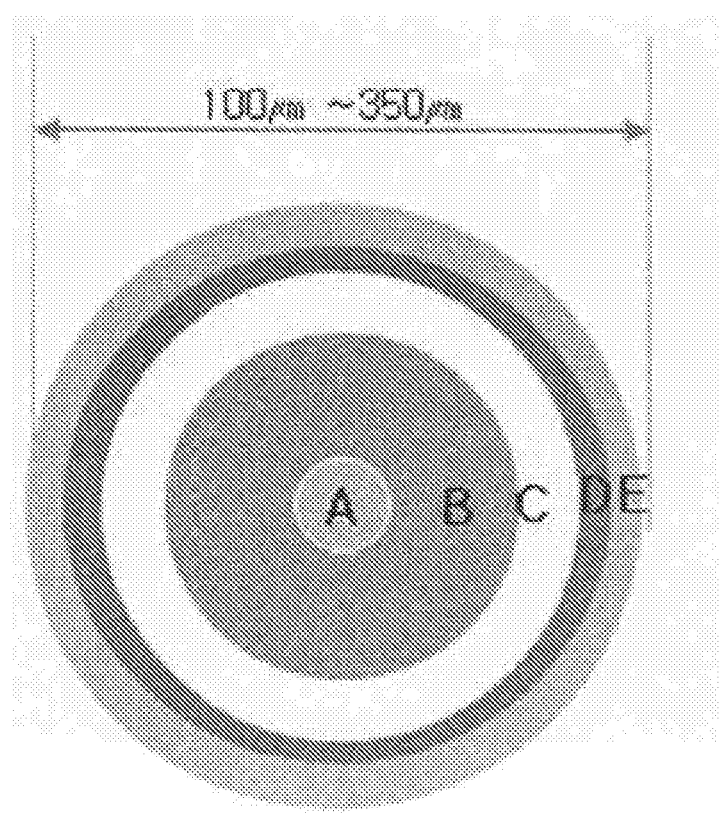
FIG. 1 is a schematic diagram illustrating a typical structure of a color-changing microcapsule of the present invention, wherein A represents a core and B, C, D and E being different layers concentrically surrounding said core.

The term "physiologically acceptable medium" is intended to denote a medium that is particularly suitable for applying a product of the invention to keratin materials, especially the skin and more particularly facial skin.

The "physiologically acceptable medium" comprises the aqueous phase used according to the present invention.

For the purposes of the present invention, the term "keratin material" is intended to cover the skin, mucous membranes such as the lips, the nails and the eyelashes. The skin and the lips, in particular facial skin, are most particularly considered according to the invention.

As emerges from the examples that follow, compositions in accordance with the invention prove to be advantageous in several aspects.

Encapsulation of the colorants prevents undesirable re-agglomeration of pigments during manufacture and prolonged storage of the cosmetic compositions.

As the microcapsules of the invention have the ability of swelling or softening in contact of an aqueous phase as defined hereunder, they are advantageously deformable when applied on a keratin material and consequently provide a soft feeling to the user. Furthermore, their low size contributes to not create any discomfort or unfavourable, grainy, feeling when applied.

However, the microcapsules of the invention are soft enough to rupture upon very slight rubbing or pressing on the skin in order to release their content but, nevertheless, are durable enough to avoid destruction of the coating during manufacture, even during an industrial process, and storage of corresponding change-color composition.

In addition, the microcapsule of the invention allows the use of regular equipment for the preparation of the compositions of the invention because no coloring of the apparatus occurs during the manufacturing process.

Accordingly, the microcapsules of the present invention are particularly interesting since they mask the original color of the encapsulated colorants, increase the stability of these colorants against degradation, and prevent undesirable release of the encapsulated colorants into the composition during the manufacturing process and prolonged storage.

At last, compositions of the invention also have the advantage of satisfying a consumer expectation in terms of cosmetic products.

According to another of its aspects, a subject of the present invention is also directed to a cosmetic process comprising at least the steps consisting in applying at least part of a composition according to the invention on the surface of a keratin material, in particular the skin.

According to the invention, the "color changing composition" means a composition wherein the color before application is different from the color after application, this difference being visible to the naked eyes.

In particular, this color changing composition may be linked to a color-difference ΔE in CIE Lab system 1976 (ΔE before/after application) value.

The ΔE is defined by the equation:

$$\Delta E^* = \sqrt{((L_1-L_2)^2 + (a_1-a_2)^2 + (b_1-b_2)^2)}:$$

wherein L1,a1,b1 are the parameters in the colorimetric space of the 1st color (composition before application) and L2,a2,b2 the ones for the 2nd color (composition after the application and homogenization on the keratinic material).

These values may be measured by spectrophotometer or with a Chromasphere (for composition applied on skin).

The color changing composition according to the invention may be characterized as having a ΔE before/after application superior to 1, in particular superior or equal to 2, preferably superior or equal to 3.

Coloring Microcapsules

The term "microcapsule", as used herein, refers to a spherical microcapsule containing at least one layered coating entrapping at least one colorant and surrounding a core chemically different from the coating. Microcapsules are distinct from microspheres, which consist of spherical homogeneous matrix.

According to an embodiment, the "at least one layered coating" is a multi-layered coating preferably an organic multi-layered coating.

The term "multi-layer microcapsule" refers to a microcapsule consisting of a core surrounded by a coating based on one or more inner layer(s) and one outer layer. The one or more inner layer(s) forming the multi-layer coating of the multi-layer microcapsule and the single outer layer of the microcapsule may be formed of the same or different wall-forming organic compound(s).

The microcapsule according to the invention comprises a core also called "inner core" surrounded by a coating based on one or more layer(s). In a preferred embodiment, the microcapsule is a 'multi-layers' microcapsule, comprising at least one inner layer and one outer layer. The one or more inner layer(s) forming the multi-layer coating of the multi-layer microcapsule and the single outer layer of the microcapsule may be formed of the same or different wall-forming organic compound(s).

In a particular embodiment the inner layer and the outer layer are formed of the same wall forming organic compounds, the core is then surrounded by a one layer coating.

In one embodiment, the outer layer does not comprise any colorant. In another embodiment, the outer layer comprises at least one colorant.

The term "wall-forming organic compound" refers to an organic compound or a combination of two or more different organic compounds as defined herein, which form a component of the layer(s) of the microcapsules. In a preferred embodiment, the 'wall-forming organic compound' comprises at least one polymer.

The term "colorant" refers to organic pigments such as synthetic or natural dyes selected from any of the well known FD&C or D&C dyes, inorganic pigments such as metal oxides, or lakes and any combination (blend) thereof. Accordingly, the colorant useful according to the present invention may be oil-soluble or oil-dispersible or with limited solubility in water.

In preferred embodiments, the colorant is an inorganic pigment, more preferably a metal oxide.

Generally, average particle sizes of up to about 800 μm in diameter of colorant microcapsules are used according to the invention. Preferably the average particle size is less than about 400 μm in diameter of the colorant microcapsules for skin care applications. Advantageously the average particle size is in the range of about 10 μm to 350 μm in diameter. Preferably, the average particle size will be from 50 μm to 800 μm, in particular from 60 μm to 600 μm, and in particular from 80 μm to 500 μm, and in particular from 100 μm to 400 μm in diameter.

In particular, the average particle size may be from 50 to 1000 Mesh (around 400 μm to 10 μm), in particular from 60 to 200 Mesh (around 250 μm to 75 μm) as measured by the sieving test method or observed by microscope.

Preferably, a composition according to the invention may comprise from 0.1% to 20% by weight and preferably from 0.5% to 15% by weight of microcapsules relative to the total weight of the said composition.

In particular for a skin care composition according to the invention, the amount of microcapsules will range from 0.1% to 5%, preferably from 0.2% to 3% by weight relative to the total weight of composition.

In particular for a make-up composition according to the invention, the amount of microcapsules will range from 0.5% to 20%, preferably from 1% to 15%, more preferably from 2% to 10% by weight relative to the total weight of composition.

According to a particular embodiment, the encapsulated colorant(s) may be present in a composition according to the invention in an amount in active matter of encapsulated pigments ranging from 0.5% to 20% by weight, in particular from 1% to 15% by weight, and more particularly from 2% to 12% by weight, of the total weight of said composition.

The microcapsules will be integrated in the cosmetic formula generally at the latest stages of the formulation and after filtering stages if any, to avoid the microcapsules being broken. Preferably, the microcapsules according to the inventions are added and mixed uniformly at temperatures under 50° C. They are mixed gently with a paddle rather than a homogenizer.

The microcapsules may be produced by several methods known to the man skilled in the art within the coating or encapsulation domain, including pelletization, granulation, coating, etc. For example, the microcapsules may be obtained by a method comprising mixture of the compounds (actives, pigments, polymers, solvents) and drying to form capsules as disclosed in WO01/35933 and WO2011/027960, or a method comprising granulation and coating by spray drying as disclosed in FR2841155, or by fluidized bed technology, which has been used in the food and pharmaceutical industry for a long time for coating and encapsulating ingredients. As an example may be cited WO2008/139053, which concerns the preparation of spheroid multilayer capsules comprising a core of sugar and concentric layers of pharmaceutical actives. Fixation of pharmaceutical actives on the core is achieved by impregnation, pulverization or projection, and then the $1^{st}$ layer is dried before application of a second one.

Fluid bed process is disclosed for example in Teunou et al. (Fluid-Bed Coating, Poncelet, 2005, D. *Food Science and Technology* (Boca Raton, Fla., United States), Volume 146 Issue Encapsulated and Powdered Foods, Pages 197-212). A specific feature of the fluid bed process is that it leads to coated particles wherein the core is well encapsulated, compared to spray drying, which leads to a matrix with the core material randomly dispersed in a polymer.

In a preferred embodiment, the microcapsules are obtained by fluid bed process.

According to this embodiment, preferably at least one layer of the microcapsules is obtained by fluid bed process.

In a particular embodiment, the outer layer is obtained by fluid bed process.

In another particular embodiment at least one inner layer is obtained by fluid process.

Most preferably, all layers are obtained by fluid bed process.

A man skilled in the art knows how to adjust air quantity, liquid quantity and temperature allowing to reproduce a capsule according to the invention.

Preferably a fluid bed process implemented according to the invention includes Würster process and/or tangential spray process. Such a process allows, contrary to a pelletization process, to prepare spherical capsules with a core surrounded by one or more circumferential layers.

When the whole process for preparing the layers surrounding the core of the microcapsules according to the invention is carried out by fluid bed process, the microcapsule layers are advantageously regular, concentric and present a homogenous thickness.

Different examples of preparation of capsules according to the invention will be given later in this description.

I a) Core

The core is made of at least an organic material. The size of said core preferably ranges from 500 nm to 150 µm in diameter.

Preferably the core is in a solid and/or crystal form at room temperature.

In a particular embodiment, the organic material is selected from organic materials having high water dissolvability. Preferably, the core is water-soluble or water-dispersible.

In a particular embodiment, the core is uncoloured, i.e. it does not contain colorant material.

In a particular embodiment, the core is based on only one compound. This compound is organic and more preferably is a natural compound.

According to a preferred embodiment, the core is sugar-alcohol, preferably a monosaccharide-polyol advantageously selected from mannitol, erythritol, xylitol, sorbitol.

In a particular embodiment, the core is made of mannitol and more preferably exclusively made of mannitol.

According to an alternative embodiment, the core contains at least mannitol and at least one additional ingredient being preferably a polymer selected from hydrophilic polymers. In particular, such a core may comprise mannitol and hydrophilic polymers chosen among cellulose polymers, starch polymers and their mixture, preferably their mixture.

In a preferred embodiment, the cellulose polymer is a carboxymethylcellulose and the starch polymer is a non-modified natural starch, for example corn starch.

The core may be constituted by a seed (or crystal) of one of the previous materials.

The core is preferably contained in an amount of from 1% to 50% by weight, preferably 4 to 40% by weight, in particular 5 to 30% by weight, and in particular from 10 to 20% by weight with respect to the total weight of the micro capsule.

The mannitol is preferably contained in an amount of from 2% to 100% by weight, preferably 5 to 100% by weight, and in particular 100% by weight with respect to the total weight of the core.

The mannitol is preferably contained in an amount of from 1% to 50% by weight, preferably 4% to 40% by weight, in particular 5% to 30% by weight, and in particular from 10% to 20% by weight with respect to the total weight of the microcapsule.

I b) External Layer(s) or Coating

As disclosed previously, the core is advantageously surrounded with a coating, or external layer(s) preferably comprising at least one inner layer and one outer layer. In this latter case, these layers preferably extend concentrically in respect with the core.

The layer(s) is/are preferably organic, i.e. contain(s) at least one organic compound as wall-forming material. Preferably, the inner and/or outer layer(s) include(s) at least one polymer, and in particular a hydrophilic polymer.

Polymer(s)

The composition according to the invention comprises one or more polymer(s). In a particular embodiment, the polymer(s) is/are hydrophilic polymer(s).

Such hydrophilic polymer(s) is/are soluble or dispersible in water or in alcohol compounds, in particular chosen from lower alcohols, glycols, polyols.

For the purposes of the present patent application, the term "hydrophilic polymer" means a (co)polymer that is capable of forming hydrogen bond(s) with water or alcohol compounds, in particular chosen from lower alcohols, glycols, polyols. In particular, polymers are concerned which are capable of forming O—H, N—H and S—H bonds.

According to a particular embodiment of the invention, the hydrophilic polymer may swell or soften in contact with water or alcohol compounds, in particular chosen from lower alcohols, glycols, polyols.

The hydrophilic polymer(s) may be chosen from the following polymer(s):

acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglycerides) sold under the name Luvigel EM by the company;

copolymers of acrylic acid and of acrylamide sold in the form of the sodium salt thereof under the names Reten by the company Hercules, the sodium polymethacrylate sold under the name Darvan No. 7 by the company Vanderbilt, and the sodium salts of polyhydroxycarboxylic acids sold under the name Hydagen F by the company Henkel;

polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol ETD 2020, and even more preferentially Pemulen TR-2;

alkylacrylic/alkylmethacrylic acid copolymers and their derivatives notably their salts and their esters, such as the copolymer of ethyl acrylate, methyl methacrylate and low content of methacrylic acid ester with quaternary ammonium groups provided under the tradename of EUDRAGIT RSPO from Evonik Degussa;

AMPS (polyacrylamidomethylpropanesulfonic acid partially neutralized with aqueous ammonia and highly crosslinked) sold by the company Clariant;

AMPS/acrylamide copolymers such as the products Sepigel or Simulgel sold by the company SEPPIC, especially a copolymer of INCI name Polyacrylamide (and) C13-14 Isoparaffin (and) Laureth-7;

polyoxyethylenated AMPS/alkyl methacrylate copolymers (crosslinked or non-crosslinked) of the type such as Aristoflex HMS sold by the company Clariant;

polysaccharides and derivatives, such as:

anionic, cationic, amphoteric or nonionic chitin or chitosan polymers;

cellulose polymers and derivatives, preferably other than alkylcellulose, chosen from hydroxyethylcellulose, hydroxypropylcellulose, hydroxymethylcellulose, ethylhydroxyethylcellulose and carboxymethylcellulose, and also quaternized cellulose derivatives; in a preferred embodiment, the cellulose polymers is a carboxymethylcellulose;

Starch polymers and derivatives, eventually modified; in a preferred embodiment, the starch polymer is a natural starch;

optionally modified polymers of natural origin, such as galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;

alginates and carrageenans;

glycoaminoglycans, hyaluronic acid and derivatives thereof;

mucopolysaccharides such as hyaluronic acid and chondroitin sulfates, and mixtures thereof;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

and the mixtures thereof.

Preferably, the composition according to the invention, and in particular the external layer(s) comprise(s) hydrophilic polymers selected from the group consisting of polysaccharides and derivatives, acrylic or methacrylic acid homopolymers or copolymers or salts and esters thereof, and their mixture.

The said polymer(s) is (are) advantageously selected from (poly)(alkyl)(meth)acrylic acid and derivatives, notably (poly)(alkyl)(meth)acrylate and derivatives, preferably from alkylacrylic/alkylmethacrylic acid copolymers and their derivatives, and most preferably is a copolymer of ethyl acrylate, methyl methacrylate and low content of methacrylic acid ester with quaternary ammonium groups provided under the tradename of EUDRAGIT RSPO from Evonik Degussa.

Said polysaccharides and derivatives are preferably selected from chitosan polymers, chitin polymers, cellulose polymers, starch polymers, galactomannans, alginates, carrageenans, mucopolysaccharides, and their derivatives, and the mixture thereof.

In a preferred embodiment, the external layer(s) is/are devoid of microcrystalline cellulose.

According to one particularly preferred embodiment, said polysaccharides and their derivatives are preferably selected from the ones including one type of ose or several type of ose(s), preferably several types of oses, in particular at least D-Glucose unit(s) as ose(s), preferably starch polymers, cellulose polymers, and derivatives, and the mixture thereof.

According to a preferred embodiment, the microcapsule contains at least one hydrophilic polymer selected from the group consisting of starch and its derivatives, in particular corn starch, cellulose and its derivatives, homo- and/or co-polymer of methacrylic acid and/or methacrylic acid ester or co-polymer of (alkyl)acrylic acid and/or (alkyl) methacrylic acid and their derivatives, preferably their salts and their ester, and in particular the capsule contains polymethyl methacrylate.

Starch usable according to the present invention is usually issued from vegetable raw materials, such as rice, soybeans, potatoes, or corn. Starch can be unmodified or (by analogy with cellulose) modified starch. In a preferred embodiment, the starch is unmodified.

Preferred homo- and/or co-polymer of methacrylic acid and/or methacrylic acid ester are those wherein the copolymer of methyl methacrylate and ethyl acrylate has a molecular weight from 750 to 850 kDa.

Cellulose derivatives include, for example, alkali celluloses carboxymethyl cellulose (CMC), cellulose esters and ethers, and aminocelluloses. In a particular embodiment, the cellulose is a carboxymethyl cellulose (CMC).

According to a preferred embodiment, the capsule contains at least starch derivative, in particular corn starch, polymethyl methacrylate, co-polymer of (alkyl)acrylic acid and/or (alkyl)methacrylic acid and their derivatives preferably their salts and their ester, and/or cellulose derivative.

Preferably, the microcapsule contains polymer(s) which are not cross-linked.

The polymer(s) may be in one or several layer(s).

In another embodiment, the polymer(s) may be in the core.

The microcapsule may contain polymer(s) in the core and/or in the layer(s).

In a particular embodiment, the polymer(s) is (are) in the core and in the layer(s).

In an embodiment, the core contains at least starch and/or cellulose derivative as polymer(s). When the starch is contained within the core, it represents the main ingredient of such a core, i.e. the weight amount of starch is greater than the respective amount of other compounds of the core.

The polymer may represent from 0.5 to 20% by weight of the microcapsule, in particular from 1 to 10% by weight, preferably from 2 to 8% by weight of the microcapsule.

The different layers forming the coating may be based on identical or different polymers. Advantageously, they will be formed from the same polymer.

In contrast, the layers will be advantageously differently coloured.

This different colour may be obtained through the use of different colorants but also the use of different concentrations in at least one colorant when the colorant will be the same for two layers.

In a particular embodiment, the outer layer contains at least one colorant.

In another embodiment, the outer layer does not contain any colorant.

Colorant(s)

As previously stated, "colorant" includes any organic or inorganic pigment or colorant approved for use in cosmetics by CTFA and the FDA used in cosmetic formulations.

Thus the term "colorant" refers to organic pigments such as synthetic or natural dyes selected from any of the well known FD&C or D&C dyes, to inorganic pigments such as metal oxides, or lakes such as the ones based on cochineal carmine, barium, strontium, calcium or aluminum and any combination (blend) thereof. Such colorants are detailed here-after.

In a particular embodiment, the colorant may be water-soluble or water-dispersible.

In another embodiment, the colorant useful according to the present invention may be oil-soluble or oil-dispersible or with limited solubility in water.

In preferred embodiments, the colorant is an inorganic pigment, more preferably a metal oxide.

Advantageously, the colorants of the multi-layer microcapsules are primary metal oxides selected from iron oxides, titanium dioxide, aluminum oxide, zirconium oxides, cobalt oxides, cerium oxides, nickel oxides, tin oxide or zinc oxide, or composite oxides, more preferably an iron oxide selected from red iron oxide, yellow iron oxide or black iron oxide, or a mixture thereof.

The layer(s) may also contain lakes corresponding to an organic colorant secured to a substrate. Such (a) lake(s) is (are) advantageously chosen among the here-below material, and their mixture(s):

carmin of cochineal;

organic pigments of azoic, anthraquinonic, indigoid, xanthenic, pyrenic, quinolinic, triphenylmethane, fluoran colorants; Among the organic pigments may be cited those known under the following trademark references: D&C Blue no 4, D&C Brown no 1, D&C Green no 5, D&C Green no 6, D&C Orange no 4, D&C Orange no 5, D&C Orange no 10, D&C Orange no 11, D&C Red no 6, D&C Red no 7, D&C Red no 17, D&C Red no 21, D&C Red no 22, D&C Red no 27, D&C Red no 28, D&C Red no 30, D&C Red no 31, D&C Red no 33, D&C Red no 34, D&C Red no 36, D&C Violet no 2, D&C Yellow no 7, D&C Yellow no 8, D&C Yellow no 10, D&C Yellow no 11, FD&C Blue no 1, FD&C Green no 3, FD&C Red no 40, FD&C Yellow no 5, FD&C Yellow no 6;

the water-insoluble salts of sodium, potassium, calcium, baryum, aluminum, zirconium, strontium, titanium, of acid colorants such as azoic, anthraquinonic, indigoids, xanthenic, pyrenic, quinolinic, triphenylmethane, fluoran colorants, these colorants may include at least one carboxylic or sulfonic acid group.

The organic lakes may also be protected by an organic support such as rosin or aluminum benzoate.

Among the organic lakes, we may in particular cite those known under the following names: D&C Red no 2 Aluminum lake, D&C Red no 3 Aluminum lake, D&C Red no 4 Aluminum lake, D&C Red no 6 Aluminum lake, D&C Red no 6 Barium lake, D&C Red no 6 Barium/Strontium lake, D&C Red no 6 Strontium lake, D&C Red no 6 Potassium lake, D&C Red no 6 Sodium lake, D&C Red no 7 Aluminum lake, D&C Red no 7 Barium lake, D&C Red no 7 Calcium lake, D&C Red no 7 Calcium/Strontium lake, D&C Red no 7 Zirconium lake, D&C Red no 8 Sodium lake, D&C Red no 9 Aluminum lake, D&C Red no 9 Barium lake, D&C Red no 9 Barium/Strontium lake, D&C Red no 9 Zirconium lake, D&C Red no 10 Sodium lake, D&C Red no 19 Aluminum lake, D&C Red no 19 Barium lake, D&C Red no 19 Zirconium lake, D&C Red no 21 Aluminum lake, D&C Red no 21 Zirconium lake, D&C Red no 22 Aluminum lake, D&C Red no 27 Aluminum lake, D&C Red no 27 Aluminum/Titanium/Zirconium lake, D&C Red no 27 Barium lake, D&C Red no 27 Calcium lake, D&C Red no 27 Zirconium lake, D&C Red no 28 Aluminum lake, D&C Red no 28 Sodium lake D&C Red no 30 lake, D&C Red no 31 Calcium lake, D&C Red no 33 Aluminum lake, D&C Red no 34 Calcium lake, D&C Red no 36 lake, D&C Red no 40 Aluminum lake, D&C Blue no 1 Aluminum lake, D&C Green no 3 Aluminum lake, D&C Orange no 4 Aluminum lake, D&C Orange no 5 Aluminum lake, D&C Orange no 5 Zirconium lake, D&C Orange no 10 Aluminum lake, D&C Orange no 17 Barium lake, D&C Yellow no 5 Aluminum lake, D&C Yellow no 5 Zirconium lake, D&C Yellow no 6 Aluminum lake, D&C Yellow no 7 Zirconium lake, D&C Yellow no 10 Aluminum lake, FD&C Blue no 1 Aluminum lake, FD&C Red no 4 Aluminum lake, FD&C Red no 40 Aluminum lake, FD&C Yellow no 5 Aluminum lake, FD&C Yellow no 6 Aluminum lake.

The chemistry material corresponding to each of these organic colorants previously cited are mentioned in the book called « International Cosmetic Ingredient Dictionary and Handbook », Edition 1997, pages 371 to 386 and 524 to 528, published by « The Cosmetic, Toiletry, and Fragrance Association », of which the content is hereby incorporated by reference in the present specification.

According to a preferred embodiment, the lake(s) is/are selected from carmin of cochineal and the water-insoluble salts of sodium, potassium, calcium, barium, aluminum, zirconium, strontium, titanium, of acid colorants such as azoic, anthraquinonic, indigoid, xanthenic, pyrenic, quinolinic, triphenylmethane, fluoran colorants, being given that these colorants may include at least one carboxylic or sulfonic acid group, and their mixture.

According to a preferred embodiment, the lake(s) is/are selected from carmin of cochineal and the water-insoluble salts of sodium, calcium, aluminum, and their mixture.

As lake incorporating carmine we may cite the commercial references: CARMIN COVALAC W 3508, CLOISONNE RED 424C et CHROMA-LITE MAGENTA CL4505.

The water-insoluble aluminum salts are preferably selected from FDC Yellow No 5 aluminum lake, le FDC Blue No 1 aluminum lake, le FDC Red No 40 aluminum lake, le FDC Red No 30 aluminum lake, le FDC Green No 5 aluminum lake, and their mixtures. As compound incorporating such inorganic lake may notably be cited the commercial references: INTENZA FIREFLY C91-1211, INTENZA AZURE ALLURE C91-1251, INTENZA THINK PINK C91-1236

The water-insoluble calcium salts are preferably selected from Red No 7 calcium lake. As compound incorporating such inorganic lake may notably be cited the commercial references: INTENZA MAGENTITUDE C91-1234, INTENZA HAUTE PINK C91-1232, INTENZA RAZZLED ROSE C91-1231, INTENZA AMETHYST FORCE C91-7231, INTENZA PLUSH PLUM C91-7441, INTENZA ELECTRIC CORAL C91-1233, FLORASOMES-JOJOBA-SMS-10% CELLINI RED-NATURAL and their mixture.

The water-insoluble sodium salts are preferably selected from Red No 6 sodium lake and Red No 28 sodium lake, and their mixture. E As compound incorporating such inorganic lake may notably be cited the commercial references: INTENZA MANGO TANGO C91-1221 and INTENZA NITRO PINK C91-1235.

In preferred embodiments, the colorant is an inorganic colorant.

In a preferred embodiment, the colorant is a metallic oxide. Such metallic oxide is preferably selected from iron oxides, titanium oxides, and mixtures thereof.

The color-changing compositions of the invention may comprise a mixture of two or more colorants, either encapsulated individually in microcapsules and/or one or more blends of colorants encapsulated within the multi-layer microcapsules.

In accordance with this specific embodiment, each layer of the microcapsule may contain at least one specific colorant or a specific blend of colorant(s).

In accordance with this specific embodiment, the color-changing composition of the invention comprises two or more microcapsules of the invention having different colors.

A person skilled in the art knows how to choose colorants and combinations of colorants to produce a desired color effect or color change.

As stated previously, the microcapsules of the invention contain preferably at least titanium dioxide and/or iron oxides in their coating, preferably at least titanium dioxide.

In a preferred embodiment, the microcapsules of the invention contain preferably at least titanium dioxide and iron oxides in their coating.

According to a specific embodiment, the outer layer of said microcapsules contains titanium dioxide and more preferably as only colorant.

According to these specific embodiments, the outer layer of said microcapsules contains titanium dioxide as the sole colorant and the composition according to the invention is non-colored, "non-colored" or "uncolored" composition meaning a transparent or white composition.

According to a preferred embodiment the composition according to the present invention, comprises uncoloured microcapsules, that is the outer layer being white or transparent, and when the outer layer is transparent, the visible inner layer is white.

For the purposes of the invention, the term "transparent composition" means a composition which transmits at least 40% of light at a wavelength of 750 nm without scattering it, i.e. a composition in which the scattering angle of the light is less than 5° and is better still about 0°.

The transparent composition may transmit at least 50%, especially at least 60% and especially at least 70% of light at a wavelength of 750 nm.

The transmission measurement is made with a Cary 300 Scan UV-visible spectrophotometer from the company Varian, according to the following protocol:
  the composition is poured into a square-sided spectrophotometer cuvette with a side length of 10 mm;
  the sample of the composition is then maintained in a thermostatically-regulated chamber at 20° C. for 24 hours;
  the light transmitted through the sample of the composition is then measured on the spectrophotometer by scanning wavelengths ranging from 700 nm to 800 nm, the measurement being made in transmission mode;
  the percentage of light transmitted through the sample of the composition at a wavelength of 750 nm is then determined.

The transparent compositions, when they are placed 0.01 m in front of a black line 2 mm thick in diameter drawn on a sheet of white paper, allow this line to be seen; in contrast, an opaque composition, i.e. a non-transparent composition, does not allow the line to be seen.

According to a specific embodiment, the outer layer of said microcapsules contains organic pigments or iron oxides.

The colorants are present in amounts ranging from 20% to 90% by weight, preferably from 30% to 80% by weight, more preferably from 50% to 75% by weight relative to the total weight of the microcapsule.

In a particular embodiment, the microcapsules contain metallic oxides selected from iron oxides, titanium oxides, and mixtures thereof, present in an amount ranging from 20% to 90% by weight, preferably from 30% to 85% by weight, more preferably from 50% to 85% by weight relative to the total weight of the microcapsule.

In particular the titanium oxide may be present from 28% to 80% by weight, preferably from 30% to 75% by weight, and more preferably from 30 to 50% by weight, relative to the total weight of the microcapsule.

In particular the iron oxides may be present from 5% to 75% by weight, preferably 8% to 65% by weight relative to the total weight of the microcapsule. In a particular embodiment, the iron oxides are present in an amount higher than 15% by weight, preferably higher than 30% by weight, and in particular from 40% to 65% by weight relative to the total weight of the microcapsule.

In a preferred embodiment, in at least one layer, and preferably in every layer, the colorants are the main ingredients, i.e. represent at least 40% by weight of the layer(s), preferably at least 75% by weight of the layer(s), more preferably at least 95% by weight of the layer(s).

In a preferred embodiment the mean thickness of the titanium dioxide layer ranges from 5 μm to 150 μm.

Lipid-Based Material

The inner and/or outer layer(s) may also include advantageously at least one lipid-based material.

According to a particular embodiment of this invention, such a lipid-based material may have amphiphilic properties, that is to say having an apolar part and a polar part.

Such lipid-based material can include at least one or several $C_{12}$-$C_{22}$ fatty acid chain(s) such as those selected from stearic acid, palmitic acid, oleic acid, linoleic acid, linolenic acid, etc., and mixtures thereof. Preferably these fatty acids chains are hydrogenated. Eventually, these fatty acid chains may be the apolar part of a lipid-based material.

Such lipid-based material is preferably selected from phospholipids. These phospholipids are preferably selected from phosphoacylglycerol, more preferably selected from lecithins, and are in particular hydrogenated lecithin.

The lipid based material may represent from 0.05 to 5% by weight of the microcapsule, in particular from 0.1 to 1% by weight of microcapsule.

By combining three or more compounds (ex: sugar alcohols, polymers, lipid-based material) in the microcapsule of different hardness and/or water solubility, it is possible to adjust the time required for colorant-encapsulated microcapsules to break down on the skin so that, by varying the method or intensity of application onto the skin, it is possible to adjust the preferred colouration or gradation pattern.

Thus, according to a preferred embodiment, the multilayer coating contains at least starch as polymer and at least one lipid-based material, which is preferably lecithin.

According to an advantageous embodiment the microcapsules according to the invention include at least one monosaccharide or its derivative and at least one polysaccharide or its derivatives.

According to a preferred embodiment, the microcapsules include a core comprising a monosaccharide derivative and a coating comprising a polysaccharide (or its derivative) including one type of ose or several type of ose(s), preferably several types of oses.

According to a more preferably embodiment, the microcapsules include a core comprising a monosaccharide polyol, preferably selected from mannitol, erythritol, xylitol, sorbitol, and a coating comprising a polysaccharide (or its derivative) including as ose(s) at least one or more D-Glucose unit(s).

According to a preferred embodiment, the microcapsules include three or more colorants in different layers.

According to a preferred embodiment, the microcapsules additionally include a lipid-based material chosen from phospholipids, advantageously selected from phosphoacylglycerol and in particular from lecithins.

In a particular embodiment, the core contains mannitol, starch polymer and cellulose derivatives and optionally a lipid-based material. In such a case, the starch polymer is the main ingredient i.e. the weight amount of starch is greater than the respective amount of mannitol, cellulose derivative and lipid-based material of the core.

Referring to FIG. 1, according to a preferred embodiment, the present invention advantageously provides a color-changing microcapsule having a size ranging from 50 μm to 800 μm, preferably from 60 μm to 500 μm in diameter of the microcapsule, comprising:
  i) a core (A), preferably having a size ranging from 500 nm to 150 μm in diameter, which preferably does not contain any colorant, and comprising at least one organic core preferably selected from at least one sugar alcohol preferably a monosaccharide-polyol advantageously selected from mannitol, erythritol, xylitol, sorbitol, and mixture thereof;

ii) one first layer (B) surrounding said core comprising:
at least one colorant, preferably iron oxide(s), and
a binder selected from at least one polymer, at least one lipid-based material, and their mixture, preferably their mixture;

iii) one second layer (C) surrounding said first layer (B), preferably having a thickness of 5 to 500 µm, comprising:
titanium dioxide particles, and
a binder selected from at least one polymer, at least one lipid-based material, and their mixture, preferably their mixture;

iv) optionally one third layer (D) surrounding said second layer (C) comprising:
at least one colorant, and
a binder selected from at least one polymer, at least one lipid-based material, and their mixture, preferably their mixture;

v) optionally one fourth layer (E) surrounding said third layer (D), if any, or surrounding said second layer (C) comprising
at least one wall-forming polymer preferably selected from polysaccharides such as cellulose derivatives, in particular cellulose ether and cellulose ester, from (poly)(alkyl)(meth)acrylic acid and derivatives, notably (poly)(alkyl)(meth)acrylate and derivatives, and preferably from alkylacrylic/alkylmethacrylic acid copolymers and their derivatives.

As examples of commercially available microcapsules to be used in the composition of the invention, we may refer to the following microcapsules produced by Korea Particle Technology KPT under the commercial names:

Magic 60-WP0105 from KPT: pink spherical microcapsule containing titanium dioxide, mannitol, hydrogenated lecithin, synthetic fluorphlogopite, red 30 lake, *zea mays* (corn) starch, tin oxide, having 60-200 Mesh particle size;

Magic50-BW0105 from KPT: ash gray spherical microcapsule containing mannitol, iron oxide red, iron oxide yellow, iron oxide black, hydrogenated lecithin, titanium dioxide, *zea mays* (corn) starch, having 60-200 Mesh particle size.

The microcapsules suitable for the present invention are stable into the compositions according to the present invention, preferably at high temperatures, for instance greater than or equal to 40° C., for example for one month, better two months and still better three months in an oven at 45° C. or for 15 days in an oven at 60° C.

In a preferred embodiment, the microcapsules according to the present invention present an appropriate softening kinetics.

That is preferably, at least three hours after being in contact with the other compounds of the formula, the hardness of the microcapsules is advantageously from 5 to 50 grams, more preferably from 6 to 20 grams and still more preferably from 7 to 10 grams. Such hardness is in conformity with an industrial process for preparing the cosmetic compositions including such microcapsules.

Such values of softening kinetics and hardness allow to provide not only aesthetic microcapsules but also overall aesthetic compositions.

Particularly, the composition may lead to different shades or color gradations depending on the intensity of the rubbing. The compositions may advantageously present a high chromaticity C* as measured in the in CIE Lab system 1976.

Aqueous Phase

The microcapsules of the invention need to be in contact with an aqueous phase comprising water and at least one compound chosen from polyols, glycols, $C_2$-$C_8$ monoalcohols, and mixtures thereof in order to be softened when applied on the keratinic material. This aqueous phase is particularly advantageous for imparting and/or improving deformability to the microcapsules of the invention.

Advantageously this aqueous phase acts as a swelling agent or as a softening agent towards the microcapsules without breaking them. The microcapsules are not inert when placed in this aqueous phase either they swell: their diameter significantly increases with an optional softening of the microcapsules, or the microcapsules significantly soften without increasing of the diameter, they become more malleable and easier to break when applied onto the skin.

The aqueous phase used in the composition according to the invention is able to act on the softening kinetics of the microcapsules and more particularly it allows to obtain a good balance between softening kinetics and hardness.

As a consequence, said aqueous phase is particularly advantageous for softening the microcapsules suitable for the present invention, in an appropriate way, since said aqueous phase plays a role on softening kinetics of said microcapsules.

The aqueous phase comprises water and, where appropriate, a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

As said, the composition of the invention contains an aqueous phase comprising water and at least one compound chosen among polyols, glycols, $C_2$-$C_8$ monoalcohols and mixtures thereof. It also may contain $C_4$ ketones and $C_2$-$C_4$ aldehydes.

The composition of the invention contains microcapsules as defined above and an aqueous phase comprising water and at least one compound chosen from polyols, glycols, $C_2$-$C_8$ monoalcohols and mixtures thereof. Preferably the aqueous phase comprises water and the at least one compound chosen from polyols, glycols and the mixtures thereof.

The aqueous phase is preferably present in an amount of at least 3% by weight, preferably at least 5% by weight, more preferably at least 8% by weight and advantageously at least 10% by weight relative to the weight of the composition.

Advantageously, the aqueous phase may be present in a content ranging from 30% to 99% by weight, preferably from 40% to 95% more preferably from 50% to 90% by weight relative to the total weight of the said composition.

Advantageously, water is present in an amount of at least 30% by weight, preferably at least 40% by weight, more preferably at least 50% by weight relative to the weight of the composition. Generally water is present in an amount ranging from 30% to 90% by weight, preferably 40% to 85% by weight and more preferably from 50 to 80% by weight, relative to the weight of the composition.

Advantageously this aqueous phase acts as a swelling agent or as a softening agent towards the microcapsules preferably without breaking them or without triggering colorant leakage.

The composition of the invention will generally comprise at least one compound chosen from polyols, glycols, $C_2$-$C_8$ monoalcohols, and mixtures thereof in amount ranging from 3% to 50% by weight, preferably from 5% to 45% by weight and more preferably from 10% to 45% by weight relative to the total weight of the composition.

In a preferred embodiment, the aqueous phase suitable for the present invention comprises at least one $C_2$-$C_8$ monoalcohols.

In another preferred embodiment, the aqueous phase suitable for the present invention comprises at least one polyol or glycol.

In another preferred embodiment, the aqueous phase suitable for the present invention comprises at least one $C_2$-$C_8$ monoalcohols and at least one polyol or glycol.

Monoalcohols or Lower Alcohols

Monoalcohol or lower alcohol that is suitable for use in the invention may be a compound of linear, branched or cyclic, saturated or unsaturated alkyl type, bearing only one —OH function.

Advantageously, $C_2$-$C_8$ monoalcohols are non cyclic monoalcohols, still preferably they are $C_2$-$C_5$ monoalcohols and preferably $C_2$-$C_3$ monoalcohols.

The lower monoalcohols that are advantageously suitable for formulating a composition according to the present invention are those especially containing from 2 to 5 carbon atoms such as ethanol, propanol, butanol, isopropanol, isobutanol preferably ethanol and/or isopropanol and more preferably at least ethanol.

A composition of the invention may comprise at least 1% by weight, preferably at least 2%, more preferably from 2% to 15%, advantageously from 3% to 10%, by weight and better still from 3% to 8% by weight, preferably from 4% to 6% by weight of mono-alcohol(s) relative to the total weight of said composition.

In a preferred embodiment, a composition of the invention comprises ethanol and/or isopropanol and more preferably at least ethanol, in a total concentration of 2 to 15% by weight and more preferably of 3 to 10% by weight relative to the total weight of said composition.

Lower monoalcohols such as ethanol can be advantageous used in many ways in the field of makeup and/or care of keratin material(s).

Such compounds are particularly useful for providing a fresh feeling to the user when he applied on the skin, a composition of the invention.

Furthermore, such a feeling of freshness, pleasant as such to the user, may also advantageously allow to activate blood circulation in the skin where it is felt, especially in the skin surrounding the eyes which forms a particularly well vascularized area. The fresh feeling accompanying the application of these lower monoalcohols thus reduces puffiness and dark circles present in this part of the face due to the high vascularity and thinness in this part of the face.

The application of lower monoalcohols can also advantageously avoid the need to apply other cooling agents such as menthol, ethyl menthane carboxamide, menthyl lactate, menthoxypropanediol around the eyes, which are generally raw material irritating to the eyes.

There is also a need to have at disposal compositions containing changing color microcapsules in a physiological medium comprising a lower alcohol because some cosmetic ingredients are particularly soluble in hydroalcoholic media.

Furthermore, the lower monoalcohols such as ethanol allow to dissolve active agents, especially keratolytic agents, such as, for example, salicylic acid and its derivatives.

Some microcapsules of the prior art rapidly disintegrate in hydroalcoholic media, as a consequence there was a need to have at disposal compositions comprising changing color microcapsules stable in hydroalcoholic media.

Polyols and Glycols

For the purposes of the present invention, the term "polyol" should be understood as meaning any organic molecule comprising at least two free hydroxyl groups. The term "polyol" according to the invention does not encompass monosaccharide-alcohol disclosed above.

Preferably, a polyol in accordance with the present invention is present in liquid form at room temperature.

The polyols/glycols are moisturizers or humectants.

They may have an effect towards the stability of other ingredients of the composition particularly towards microcapsules of the prior art.

There is thus a need to have at disposal stable compositions containing changing color microcapsules in a physiological medium comprising a polyol and/or a glycol because these compositions present a noticeable moisturizing or humecting effect.

This technical problem is solved by the compositions according to the invention. A polyol that is suitable for use in the invention may be a compound of linear, branched or cyclic, saturated or unsaturated alkyl type, bearing on each alkyl chain at least two —OH functions, in particular at least three —OH functions and more particularly at least four —OH functions.

The polyols that are advantageously suitable for formulating a composition according to the present invention are those especially containing from 2 to 32 carbon atoms preferably 2 to 20 carbon atoms and more preferably 2 to 16 carbon atoms, advantageously 2 to 10 carbon atoms, more advantageously 2 to 6 carbon atoms.

According to another embodiment, a polyol that is suitable for use in the invention may be advantageously chosen from polyethylene glycols.

According to one embodiment, a composition of the invention may comprise a mixture of polyols.

Advantageously, the polyol may be chosen from polyhydric alcohols, preferably of $C_2$-$C_8$ and more preferably $C_3$-$C_6$. The polyol may be chosen from glycerol, pentaerythritol, trimethylolpropane, ethylene glycol, propylene glycol, 1,3-butylene glycol, 1,3-propanediol, pentylene glycol, hexylene glycol, isoprene glycol, dipropylene glycol, diethylene glycol and diglycerol, ethylhexylglycerine, caprylyl glycol and mixtures thereof, glycerol and derivatives thereof, polyglycerols, such as glycerol oligomers, for instance diglycerol, and polyethylene glycols, glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

Particularly, the polyol is selected from the group consisting in glycerol, glycols, preferably propylene glycol, butylene glycol, pentylene glycol, hexylene glycol, dipropylene glycol, diethylene glycol, ethylhexylglycerine, caprylyl glycol, glycol ethers, preferably mono-, di- or tripropylene glycol of alkyl(C1-C4)ether or mono-, di- or triethylene glycol of alkyl(C1-C4)ether, and mixtures thereof.

According to one preferred embodiment of the invention, the said polyol is chosen from ethylene glycol, pentaerythritol, trimethylolpropane, propylene glycol, butylene glycol, glycerol, polyglycerols and polyethylene glycols, and mixtures thereof.

In a particular embodiment, the polyol is selected from the group consisting in glycerol, and glycols chosen from propylene glycol, butylene glycol, ethylhexylglycerine, caprylyl glycol and mixtures thereof.

According to one particular embodiment, the composition of the invention comprises at least butylene glycol, glycerol or a mixture thereof.

In a preferred embodiment, the composition comprises at least glycerol.

According to one particular embodiment, the composition of the invention comprises glycerol as sole polyol.

Advantageously the composition may comprise from 1 to 10, preferably from 2 to 8 weight percent of glycerol based on the total weight of the composition Advantageously the composition may comprise from 1 to 10, preferably from 2 to 8 weight percent of butylene glycol based on the total weight of the composition.

Advantageously the composition may comprise from 1 to 10, preferably from 2 to 8 weight percent of propylene glycol based on the total weight of the composition.

When the composition comprises glycerol and at least one glycol, the weight ratio of glycerol/glycol is advantageously from 1/2 to 3/2, preferably from 2/3 to 1/1 more preferably around 1.

In a preferred embodiment, the composition comprises glycerol and at least one glycol chosen from propylene glycol, butylene glycol, ethylhexylglycerine, caprylyl glycol, the weight ratio of glycerol/glycol is advantageously from 1/2 to 3/2, preferably from 2/3 to 1/1 more preferably around 1.

A composition according to the invention may advantageously comprise at least 10% by weight, preferably between 10 and 45% by weight and in particular between 10% and 40% by weight of polyol(s) and/or glycols, preferably one $C_2$-$C_{32}$ polyol and/or glycol, based on weight of the composition.

A composition according to the invention may advantageously comprise at least 10% by weight, preferably from 12% to 50% by weight and in particular from 13% to 40%, more preferably from 14 to 35% and better from 15% to 30% by weight of polyol(s) and/or glycols based on weight of the composition.

A composition according to the invention may advantageously comprise at least 10% by weight, preferably from 12% to 50% by weight and in particular from 13% to 40%, more preferably from 14 to 35% and better from 15% to 30% by weight of polyol(s) and/or glycols based on weight of the aqueous phase.

Preferably the polyol is a $C_2$-$C_{32}$ polyol and/or glycol.

Advantageously the weight ratio of polyol and glycol/composition is from 1/10 to 1/2 preferably from 1/8 to 1/3, more preferably from 1/6 to 1/4. More particularly the weight ratio of polyol and glycol/aqueous phase is from 1/10 to 1/2 preferably from 1/8 to 1/3, more preferably from 1/6 to 1/4.

Hydrophilic Gelifying Agent(s)

Hydrophilic gelifying agents that may be mentioned in particular include water-soluble or water-dispersible thickening polymers. These polymers may be chosen especially from:

modified or unmodified carboxyvinyl polymers, such as the products sold under the name Carbopol (CTFA name: Carbomer) by the company Goodrich; polyacrylates polymethacrylates such as the products sold under the names Lubrajel and Norgel by the company Guardian or under the name Hispagel by the company Hispano Chimica;

polyacrylamides; optionally crosslinked and/or neutralized 2-acrylamido-2-methylpropanesulfonic acid polymers and copolymers, for instance the poly(2-acrylamido-2-methylpropanesulfonic acid) sold by the company Clariant under the name Hostacerin AMPS (CTFA name: ammonium polyacryldimethyltauramide);

crosslinked anionic copolymers of acrylamide and of AMPS, which are in the form of a W/O emulsion, such as those sold under the name Sepigel 305 (CTFA name: Polyacrylamide/C13-14 isoparaffin/Laureth-7) and under the name Simulgel 600 (CTFA name: Acrylamide/Sodium acryloyldimethyltaurate copolymer/Isohexadecane/Polysorbate 80) by the company SEPPIC;

polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulose and hydroxypropylcellulose; and mixtures thereof. Preferably, these polymers may be chosen from Acrylates/C10-30 Alkyl Acrylate Crosspolymer such as, Carbopol ultrez 20, Carbopol ultrez 21, Permulen TR-1, Permulen TR-2, Carbopol 1382, Carbopol ETD 2020, Carbomer such as Synthalen K, carbopol 980, Ammonium acryloyldimethyl Taurate/Steareth-8 Methacrylate copolymer such as Aristoflex SNC, Acrylates copolymer such as Carbopol Aqua SF-1, Ammonium acryloyldimethyl taurate/steareth-25 Methacrylate Crosspolymer such as Aristoflex HMS, Ammonium acryloyldimethyl taurate such as Arisfoflex AVC, and xanthan gum such as Keltrol CG, etc, and also any polymers which contribute not only to sustain a proper viscosity, to further make capsule suspension very well and further to make it stable in shelf lives, but also to deliver a transparency.

According to a specific embodiment, the aqueous phase of the composition contains at least one neutralized 2-acrylamido-2-methylpropanesulfonic acid polymers and copolymers and one polysaccharide biopolymer.

Preferably, the hydrophilic gelifying agents suitable in the present invention include carboxyvinyl polymers such as the Carbopol products (carbomers) such as Carbopol Ultrez 20 Polymer® marketed by Lubrizol and the Pemulen products (acrylate/$C_{10}$-$C_{30}$-alkylacrylate copolymer); polyacrylamides, for instance the crosslinked copolymers marketed under the trademarks Sepigel 305 (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark Hostacerin AMPS (CTFA name: ammonium polyacryloyldimethyltaurate) or Simulgel 800 marketed by SEPPIC(CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; and mixtures thereof.

More preferably, the hydrophilic gelifying agents are chosen among an acrylate/$C_{10}$-$C_{30}$-alkylacrylate copolymer, carbomer, xanthan gum, carboxyvinylic polymer synthesized in methylene chloride, and ammonium polyacryloyldimethyltaurate, and mixtures thereof.

These gelifying agents may be present in an amount ranging for example from 0.001 to 10% by weight, preferably 0.01 to 5% by weight and more preferably from 0.05 to 3% by weight relative to the total weight of said composition.

Cosmetic Medium and Additional Ingredients

The composition according to the invention is cosmetically acceptable that is it contains a physiologically acceptable medium which is non toxic and appropriate to be applied on the keratin material of human beings.

"Cosmetically acceptable" in the sense of the present invention means a composition with pleasant appearance, odor or feeling.

The "physiologically acceptable medium" is generally adapted to the form of under which the composition is intended to be conditioned.

Particularly the nature and the amount of the ingredients are adapted for example depending on whether the composition is formulated as a solid, a fluid or a powder.

Depending upon the form and the aim of the skin care or make-up preparation, the composition of the invention will comprise, in addition to the microcapsules containing colorant, further additional cosmetic ingredient(s) such as the ones selected from volatile and non-volatile silicon or hydrocarbon oils, surfactants, fillers, thickening agents, film forming agents, polymers, preservatives, silicone elastomer, self-tanning agents, additional non-entrapped colorants, actives, UV filters, perfumes, pH regulators and mixtures thereof.

The pH of the cosmetic composition according to the present invention ranges preferably from 6.5 to 7.5. A preferred base to modify the pH is triethanolamine.

It is a matter of routine operations for a person skilled in the art to adjust the nature and amount of the additives present in the compositions in accordance with the invention such that the desired cosmetic properties thereof are not thereby affected.

Some of these conventional ingredients are detailed hereafter.

Liquid Fatty Phase

Thus, a composition according to the invention may comprise at least one fatty phase that is liquid at room temperature and atmospheric pressure, and especially at least one oil as mentioned below.

Specifically, the presence of at least one oil is advantageous insofar as it facilitates the application of the composition and affords emollience.

According to the present invention, the term "oil" means a water-immiscible non-aqueous compound that is liquid at room temperature (25° C.) and at atmospheric pressure (760 mmHg).

An oily phase that is suitable for preparing an anhydrous cosmetic composition according to the invention may comprise hydrocarbon-based oils, silicone oils, fluoro oils or non-fluoro oils, or mixtures thereof.

The oils may be volatile or non-volatile.

They may be of animal, plant, mineral or synthetic origin. According to one embodiment variant, oils of plant origin are preferred.

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits inclusive.

The term "non-volatile oil" means an oil that remains on the skin or the keratin fibre at room temperature and atmospheric pressure. More specifically, a non-volatile oil has an evaporation rate strictly less than 0.01 mg/cm$^2$/min.

To measure this evaporation rate, 15 g of oil or oil mixture to be tested are placed in a crystallizing dish 7 cm in diameter, placed on a balance that is in a large chamber of about 0.3 m$^3$ which is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

Advantageously, an anhydrous composition of the invention may comprise from 10% to 50% by weight and preferably from 20% to 40% by weight of oil(s) relative to the total weight of the said composition.

a) Volatile Oils

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®, or especially linear $C_8$-$C_{14}$ alkanes.

Volatile oils that may also be used include volatile silicones, for instance volatile linear or cyclic silicone oils, especially those with a viscosity ≤8 centistokes (cSt) (8×10$^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

Advantageously, a liquid fatty phase of the invention may comprise from 1% to 50% by weight, preferably from 2% to 40% by weight and better still from 5% to 30% by weight of volatile oil(s) relative to the total weight of the said liquid fatty phase.

b) Non-Volatile Oils

The non-volatile oils may be chosen especially from nonvolatile hydrocarbon-based, fluoro and/or silicone oils.

Non-volatile hydrocarbon-based oils that may especially be mentioned include:

hydrocarbon-based oils of animal origin,
hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, *calendula* oil, camellina oil, canola oil, carrot oil, safflower oil, flax oil, rapeseed oil, cotton oil, coconut oil, marrow seed oil, wheatgerm oil, jojoba oil, lily oil, *macadamia* oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyol 810®, 812® and 818® by the company Dynamit Nobel;
linear or branched hydrocarbons, of mineral or synthetic origin, such as liquid paraffins and derivatives thereof, petroleum jelly, polydecenes, polybutenes, hydrogenated polyisobutene such as Parleam, and squalane,
synthetic ethers containing from 10 to 40 carbon atoms, such as dicaprylyl ether;
synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \geq 10$. The esters may be chosen especially from esters of alcohol and of fatty acid, for instance cetostearyl octanoate, esters of isopropyl alcohol, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate.
polyol esters and pentaerythritol esters, for instance dipentaerythrityl tetrahydroxystearate/tetraisostearate,
esters of diol dimers and of diacid dimers, such as Lusplan DD-DA5® and Lusplan DD-DA7® sold by the company Nippon Fine Chemical and described in patent application US 2004-175 338,
copolymers of a diol dimer and of a diacid dimer and esters thereof, such as dilinoleyl diol dimer/dilinoleic dimer copolymers and esters thereof, for instance Plandool-G,
copolymers of polyols and of diacid dimers, and esters thereof, such as Hailuscent ISDA or the dilinoleic acid/butanediol copolymer,
fatty alcohols that are liquid at room temperature, with a branched and/or unsaturated carbon-based chain containing from 12 to 26 carbon atoms, for instance 2-octyldodecanol, isostearyl alcohol and oleyl alcohol,
$C_{12}$-$C_{22}$ higher fatty acids, such as oleic acid, linoleic acid or linolenic acid, and mixtures thereof,
dialkyl carbonates, the two alkyl chains possibly being identical or different, such as dicaprylyl carbonate sold under the name Cetiol CC® by Cognis,
oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, esters of branched $C_{24}$-$C_{28}$ fatty alcohols or fatty acids, such as those described in patent U.S. Pat. No. 6,491,927, and pentaerythritol esters, and especially triisoarachidyl citrate, glyceryl triisostearate, glyceryl tris(2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, dimethicones or phenyl trimethicones with a viscosity of less than or equal to 100 cSt, and mixtures thereof; and also mixtures of these various oils, and
mixtures thereof.

According to one embodiment, the composition of the invention comprises at least one non-volatile oil chosen from non-volatile hydrocarbon-based oils such as:
hydrocarbon-based oils of animal origin;
hydrocarbon-based oils of plant origin;
synthetic ethers containing from 10 to 40 carbon atoms;
synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \geq 10$;
polyol esters and pentaerythritol esters;
fatty alcohols that are liquid at room temperature, with a branched and/or unsaturated carbon-based chain containing from 12 to 26 carbon atoms;
dialkyl carbonates, the two alkyl chains possibly being identical or different;
oils of high molar mass; and
mixtures thereof.

Advantageously, a liquid fatty phase of the invention may comprise at least 40% by weight, preferably at least 60% by weight or even 100% by weight of non-volatile oil(s) relative to the total weight of the said liquid fatty phase.

The composition according to the invention may be anhydrous or non-anhydrous.

In anhydrous compositions according to the invention, the "at least one compound chosen from polyols, glycols, $C_2$-$C_8$ monoalcohols, and mixtures thereof" is present in an amount of at least 3% by weight, preferably at least 5% by weight, more preferably at least 8% by weight and advantageously at least 10% by weight relative to the weight of the composition, and the composition is devoid of water.

"Devoid of water" means that the composition comprises less than 3% preferably less than 1% more preferably less than 0.5% of water and is especially free of water.

Where appropriate, such small amounts of water may especially be introduced by ingredients of the composition that may contain residual amounts thereof.

In non-anhydrous compositions according to the invention, the "at least one compound chosen from polyols, glycols, $C_2$-$C_8$ monoalcohols, and mixtures thereof" is advantageously present in an amount of at least 10% by weight, preferably at least 12% by weight, more preferably at least 15% by weight relative to the weight of the composition.

Tanning Agents

For the purposes of the present invention, the expression "skin self-tanning agent" means a compound that is capable of producing, on contact with the skin, a coloured reaction with the free amine functions present in the skin, such as amino acids, peptides or proteins.

Other characteristics, aspects and advantages of the present invention will emerge on reading the detailed description that follows.

The self-tanning agents are generally chosen from certain monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in patent application FR 2 466 492 and WO 97/35842, dihydroxyacetone (DHA), and 4,4-dihydroxypyrazolin-5-ones as described in patent application EP 903 342. DHA will preferably be used.

DHA may be used in free and/or encapsulated form, for example in lipid vesicles such as liposomes, especially described in patent application WO 97/25970.

The self-tanning agent(s) is (are) generally present in proportions ranging from 0.1% to 15% by weight, preferably from 0.2% to 10% by weight and more preferentially from 1% to 8% by weight relative to the total weight of the composition.

Silicone Elastomers

According to the present invention, compositions may comprise at least one silicone elastomer. Any suitable silicone elastomer can be used in accordance with the present invention. Suitable silicone elastomers include, for example, emulsifying silicone elastomers such as polyglycerolated and/or hydrophilic emulsifying silicone elastomers such as alkoxylated silicone elastomers, and non-emulsifying silicone elastomers. Such silicone elastomers can be spherical or non-spherical.

Polyglycerolated Silicone Elastomers

Suitable polyglycerolated silicone elastomers include, for example, crosslinked elastomeric organopolysiloxanes that may be obtained by a crosslinking addition reaction of diorganopolysiloxane containing at least one hydrogen atom linked to silicon and of polyglycerolated compounds containing ethylenically unsaturated groups, especially in the presence of a platinum catalyst.

Polyglycerolated silicone elastomers that may be used include, but are not limited to, those sold under the names "KSG-710", "KSG-810", "KSG-820", "KSG-830" and "KSG-840" by the company Shin-Etsu. Suitable polyglycerolated silicone elastomers are also disclosed in U.S. Ser. No. 11/085,509, filed Mar. 22, 2005 (published as U.S. patent application publication no. 2005/0220728), the entire disclosure of which is hereby incorporated by reference.

Hydrophilic Emulsifying Silicone Elastomers

The term "hydrophilic emulsifying silicone elastomer" means a silicone elastomer comprising at least one hydrophilic chain other than a polyglycerolated chain as described above.

In particular, the hydrophilic emulsifying silicone elastomer may be chosen from polyoxyalkylenated silicone elastomers.

Suitable polyoxyalkylenated elastomers are described in patents U.S. Pat. No. 5,236,986, U.S. Pat. No. 5,412,004, U.S. Pat. No. 5,837,793 and U.S. Pat. No. 5,811,487.

Suitable polyoxyalkylenated silicone elastomers that may be used include those sold under the names "KSG-21", "KSG-20", "KSG-30", "KSG-31", "KSG-32", "KSG-33", "KSG-210", "KSG-310", "KSG-320", "KSG-330", "KSG-340" and "X-226146" by the company Shin-Etsu, or "DC9010" and "DC9011" by the company Dow Corning.

Suitable hydrophilic emulsifying silicone elastomers are also disclosed in U.S. Ser. No. 11/085,509, filed Mar. 22, 2005 (published as U.S. patent application publication no. 2005/0220728).

Non-Emulsifying Silicone Elastomers

The term "non-emulsifying" defines elastomers not containing a hydrophilic chain, such as polyoxyalkylene or polyglycerolated units.

The non-emulsifying silicone elastomer is preferably an elastomeric crosslinked organopolysiloxane that may be obtained by a crosslinking addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking coupling reaction between a diorganopolysiloxane containing hydroxyl end groups and a diorganopolysiloxane containing at least one hydrogen linked to silicon, especially in the presence of an organotin compound; or by a crosslinking coupling reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Suitable non-emulsifying silicone elastomers are described in patent applications JP61-194009 A, EP0242219 A, EP0295886 A and EP0765656 A.

Suitable non-emulsifying silicone elastomers that may be used include, but are not limited to, those sold under the names "DC 9040", "DC 9041", "DC 9509", "DC 9505" and "DC 9506" by the company Dow Corning.

Suitable non-emulsifying silicone elastomers are also disclosed in U.S. Ser. No. 11/085,509, filed Mar. 22, 2005 (published as U.S. patent application publication no. 2005/0220728).

The non-emulsifying silicone elastomer may also be in the form of elastomeric crosslinked organopolysiloxane powder coated with silicone resin, especially with silsesquioxane resin, as described, for example, in patent U.S. Pat. No. 5,538,793, the entire content of which is herein incorporated by reference. Such elastomers are sold under the names "KSP-100", "KSP-101", "KSP-102", "KSP-103", "KSP-104" and "KSP-105" by the company Shin-Etsu.

Other elastomeric crosslinked organopolysiloxanes in the form of powders include hybrid silicone powders functionalized with fluoroalkyl groups, sold especially under the name "KSP-200" by the company Shin-Etsu; hybrid silicone powders functionalized with phenyl groups, sold especially under the name "KSP-300" by the company Shin-Etsu.

The silicone elastomer may be present in the compositions of the present invention in an amount of from 0.1% to 95% by weight, preferably from 0.1% to 75% by weight, more preferably from 0.1 to 50% by weight, more preferably from 0.1% to 40% by weight, more preferably from 0.5% to 30% by weight, more preferably from 0.5% to 25% by weight, more preferably from 1% to 20%, more preferably from 1% to 15% and even more preferably from 3% to 10% by weight based on the weight of the composition.

Film-Forming Agents

Silicone Polyamide

The compositions according to the invention comprise at least one silicone polyamide.

The silicone polyamides of the composition are preferably solid at room temperature (25° C.) and atmospheric pressure (760 mmHg).

The silicone polyamides of the composition of the invention may be polymers of the polyorganosiloxane type, for instance those described in documents U.S. Pat. No. 5,874,069, U.S. Pat. No. 5,919,441, U.S. Pat. No. 6,051,216 and U.S. Pat. No. 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

A) According to a first variant, the silicone polymers are polyorganosiloxanes as defined above in which the amide units are located in the polymer chain.

The silicone polyamides may be more particularly polymers comprising at least one unit corresponding to the general formula I:

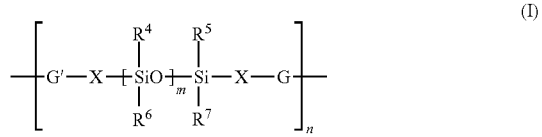
(I)

1) in which: G' represents C(O) when G represents —C(O)—NH—Y—NH—, and G' represents —NH— when G represents —NH—C(O)—Y—C(O)—, 2) $R^4$, $R^5$, $R^6$ and $R^7$, which may be identical or different, represent a group chosen from:
   linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
   $C_6$-$C_{10}$ aryl groups, optionally substituted with one or more $C_1$-$C_4$ alkyl groups,
   polyorganosiloxane chains possibly containing one or more oxygen, sulfur and/or nitrogen atoms, 3) the groups X, which may be identical or different, represent a linear or branched $C_1$ to $C_{30}$ alkylenediyl group, possibly containing in its chain one or more oxygen and/or nitrogen atoms;

4) Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl and $C_1$ to $C_6$ aminoalkyl groups, or 5) Y represents a group corresponding to the formula:

in which:
   T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
   $R^8$ represents a linear or branched $C_{10}$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

6) n is an integer ranging from 2 to 500 and preferably from 2 to 200, and m is an integer ranging from 1 to 1000, preferably from 1 to 700 and better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups. According to another embodiment, 80% of the groups $R^4$, $R^5$, $R^6$ and $R^7$ of the polymer are methyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) branched $C_{30}$ to $C_{56}$ alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

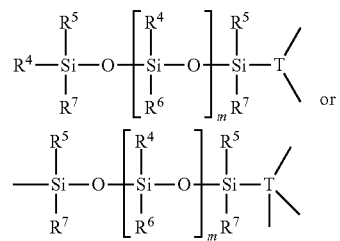

in which $R^4$, $R^5$, $R^6$, $R^7$, T and m are as defined above.

B) According to the second variant, the silicone polyamides may be polymers comprising at least one unit corresponding to formula (II):

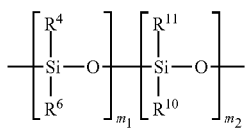 (II)

in which:
R$^4$ and R$^6$, which may be identical or different, are as defined above for formula (I),
R$^{10}$ represents a group as defined above for R$^4$ and R$^6$, or represents a group of formula —X-G"-R$^{12}$ in which X is as defined above for formula (I) and R$^{12}$ represents a hydrogen atom or a linear, branched or cyclic, saturated or unsaturated, C$_1$-C$_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more C$_1$-C$_4$ alkyl groups,
and G" represents —C(O)NH— and —HN—C(O)—,
R$^{11}$ represents a group of formula —X-G"-R$^{12}$ in which X, G" and R$^{12}$ are as defined above,
m$_1$ is an integer ranging from 1 to 998, and
m$_2$ is an integer ranging from 2 to 500.

According to the invention, the silicone polymer may be a homopolymer, i.e. a polymer comprising several identical units, in particular units of formula (I) or of formula (II).

According to the invention, it is also possible to use a silicone polymer formed from a copolymer comprising several different units of formula (I), i.e. a polymer in which at least one of the groups R$^4$, R$^5$, R$^6$, R$^7$, X, G, Y, m and n is different in one of the units. The copolymer may also be formed from several units of formula (II), in which at least one of the groups R$^4$, R$^6$, R$^{10}$, R$^{11}$, m$_1$ and m$_2$ is different in at least one of the units.

It is also possible to use a polymer comprising at least one unit of formula (I) and at least one unit of formula (II), the units of formula (I) and the units of formula (II) possibly being identical to or different from each other.

These copolymers may be block polymers or grafted polymers.

In this first embodiment of the invention, the silicone polymer may also consist of a grafted copolymer. Thus, the polyamide containing silicone units may be grafted and optionally crosslinked with silicone chains containing amide groups. Such polymers may be synthesized with trifunctional amines.

According to one advantageous embodiment of the invention, the groups capable of establishing hydrogen interactions are amide groups of formulae —C(O)NH— and —HN—C(O)—. In this case, the structuring agent may be a polymer comprising at least one unit of formula (III) or (IV):

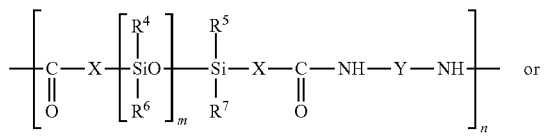 (III)

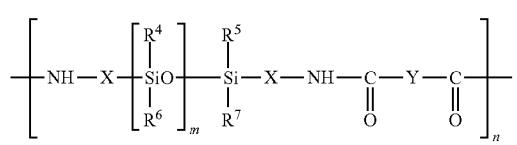 (IV)

in which R$^4$, R$^5$, R$^6$, R$^7$, X, Y, m and n are as defined above.

In these polyamides of formula (III) or (IV), m is in the range from 1 to 700, in particular from 15 to 500 and especially from 50 to 200, and n is in particular in the range from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following members:
1) 1 to 5 amide, urea, urethane or carbamate groups,
2) a C$_5$ or C$_6$ cycloalkyl group, and
3) a phenylene group optionally substituted with 1 to 3 identical or different C$_1$ to C$_3$ alkyl groups.

In formulae (III) and (IV), the alkylene groups may also be substituted with at least one member chosen from the group consisting of:
a hydroxyl group,
a C$_3$ to C$_8$ cycloalkyl group,
one to three C$_1$ to C$_{40}$ alkyl groups,
a phenyl group optionally substituted with one to three C$_1$ to C$_3$ alkyl groups,
a C$_1$ to C$_3$ hydroxyalkyl group, and
a C$_1$ to C$_6$ aminoalkyl group.

In these formulae (III) and (IV), Y may also represent:

in which R$^8$ represents a polyorganosiloxane chain and T represents a group of formula:

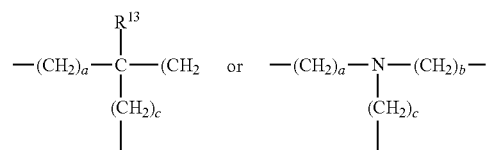

in which a, b and c are, independently, integers ranging from 1 to 10, and R$^{13}$ is a hydrogen atom or a group such as those defined for R$^4$, R$^5$, R$^6$ and R$^7$.

In formulae (III) and (IV), R$^4$, R$^5$, R$^6$ and R$^7$ preferably represent, independently, a linear or branched C$_1$ to C$_{40}$ alkyl group, preferably a CH$_3$, C$_2$H$_5$, n-C$_3$H$_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

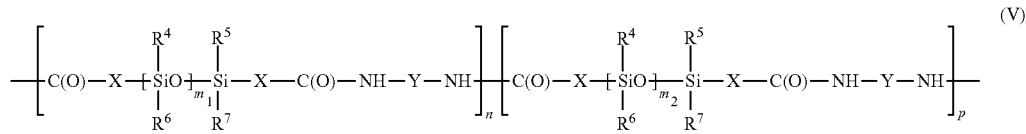

in which X, Y, n and $R^4$ to $R^7$ have the meanings given above, $m_1$ and $m_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

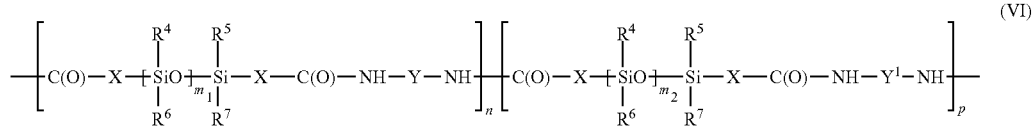

in which $R^4$ to $R^7$, X, Y, $m_1$, $m_2$, n and p have the meanings given above and $Y^1$ is different from Y but chosen from the groups defined for Y. As previously, the various units may be structured to form either a block copolymer, or a random copolymer or an alternating copolymer.

In this first embodiment of the invention, the structuring agent may also consist of a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

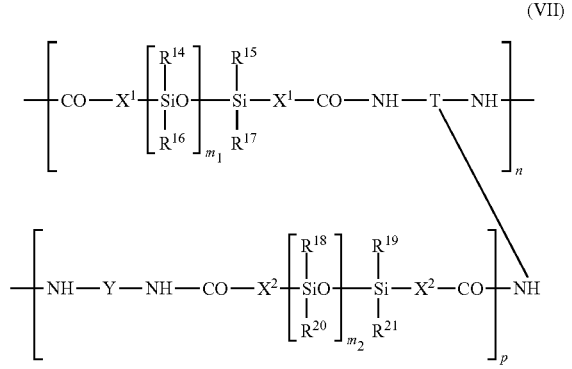

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as $R^4$ to $R^7$, $m_1$ and $m_2$ are numbers in the range from 1 to 1000, and p is an integer ranging from 2 to 500.

In formula (VII), it is preferred that:

p is in the range from 1 to 25 and better still from 1 to 7, $R^{14}$ to $R^{21}$ are methyl groups, T corresponds to one of the following formulae:

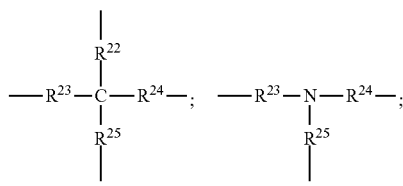

-continued

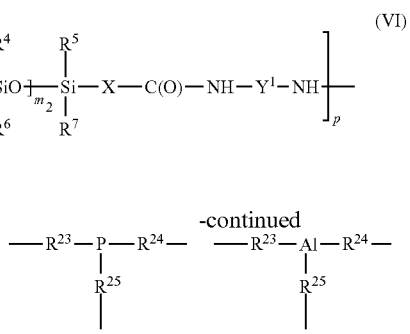

in which $R^{22}$ is a hydrogen atom or a group chosen from the groups defined for $R^4$ to $R^7$, and $R^{23}$, $R^{24}$ and $R^{25}$ are, independently, linear or branched alkylene groups, and more preferably correspond to the formula:

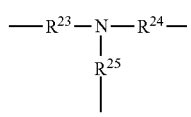

in particular with $R^{23}$, $R^{24}$ and $R^{25}$ representing —$CH_2$—$CH_2$—, $m_1$ and $m_2$ are in the range from 15 to 500 and better still from 15 to 45, $X^1$ and $X^2$ represent —$(CH_2)_{10}$—, and Y represents —$CH_2$—.

These polyamides containing a grafted silicone unit of formula (VII) may be copolymerized with polyamide-silicones of formula (II) to form block copolymers, alternating copolymers or random copolymers. The weight percentage of grafted silicone units (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (III) or (IV) and hydrocarbon-based polyamide units, may be used. In this case, the polyamide-silicone units may be located at the ends of the hydrocarbon-based polyamide.

According to one preferred embodiment, the silicone polyamide comprises units of formula III, preferably in which the groups $R^4$, $R^5$, $R^6$ and $R^7$ represent methyl groups, one from among X and Y represents an alkylene group of 6 carbon atoms and the other represents an alkylene group of 11 carbon atoms, n representing the degree of polymerization DP of the polymer.

Examples of such silicone polyamides that may be mentioned include the compounds sold by the company Dow Corning under the name DC 2-8179 (DP 100) and DC 2-8178 (DP 15), the INCI name of which is Nylon-611/dimethicone copolymers.

Advantageously, the silicone polyamides are compounds having the INCI name Nylon-611/dimethicone copolymers.

Advantageously, the composition according to the invention comprises at least one polydimethylsiloxane block polymer of general formula (I) with an index m of about 100. The index "m" corresponds to the degree of polymerization of the silicone part of the polymer.

More preferably, the composition according to the invention comprises at least one polymer comprising at least one unit of formula (III) in which m ranges from 50 to 200, in particular from 75 to 150 and is more particularly about 100.

Preferably also, $R^4$, $R^5$, $R^6$ and $R^7$ independently represent, in formula (III), a linear or branched $C_1$-$C_{40}$ alkyl group, preferably a $CH_3$, $C_2H_5$, n-$C_3H_7$ or isopropyl group.

As examples of polymers that may be used, mention may be made of one of the silicone polyamides obtained in accordance with Examples 1 to 3 of document U.S. Pat. No. 5,981,680.

Preferably, the nylon-611/dimethicone copolymer sold under the reference DC 2-8179 by Dow Corning is used as silicone polyamide.

The silicone polyamide may be present in the composition in a total content ranging from 0.5% to 45% by weight relative to the total weight of the composition, preferably ranging from 1% to 30% by weight and better still ranging from 2% to 20% by weight relative to the total weight of said composition.

Silicone Resin

Examples of these silicone resins that may be mentioned include:
- siloxysilicates, which may be trimethylsiloxysilicates of formula $[(CH_3)_3SiO]_x(SiO_{4/2})_y$ (units MQ) in which x and y are integers ranging from 50 to 80,
- polysilsesquioxanes of formula $(CH_3SiO_{3/2})_x$ (units T) in which x is greater than 100 and at least one of the methyl radicals of which may be substituted with a group R as defined above,
- polymethylsilsesquioxanes, which are polysilsesquioxanes in which none of the methyl radicals is substituted with another group. Such polymethylsilsesquioxanes are described in document U.S. Pat. No. 5,246,694.

As examples of commercially available polymethylsilsesquioxane resins, mention may be made of those sold:
  by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or
  by the company Shin-Etsu under the reference KR-220L, which are composed of units T of formula $CH_3SiO_{3/2}$ and contain Si—OH (silanol) end groups, under the reference KR-242A, which comprise 98% of units T and 2% of dimethyl units D and contain Si—OH end groups, or under the reference KR-251, comprising 88% of units T and 12% of dimethyl units D and contain Si—OH end groups.

Siloxysilicate resins that may be mentioned include trimethyl siloxysilicate resins (TMS) optionally in the form of powders. Such resins are sold under the reference SR1000 by the company Momentive Performance Materials or under the reference TMS 803 by the company Wacker. Mention may also be made of trimethyl siloxysilicate resins sold in a solvent such as cyclomethicone, sold under the name KF-7312J by the company Shin-Etsu or DC 749 and DC 593 by the company Dow Corning.

Advantageously, the silicone resin, for instance the trimethyl siloxysilicate resin, is present in a content ranging from 0.5% to 30%, or better still from 1% to 25% or even better still from 5% to 25% relative to the total weight of the composition.

Preferably, nylon-611/dimethicone is used as silicone polyamide and a trimethyl siloxysilicate resin is used as silicone resin.

According to another embodiment, the silicone resins are propylphenylsilsesquioxane resins.

Silsesquioxane resins are a specific form of film forming silicone resins. Silicone resins are crosslinked organopolysiloxanes which are solid at room temperature and generally soluble in organic solvents. When they are soluble in volatile solvents, silicone resins are capable of forming a film once the solvent has evaporated. Furthermore, if the solvent dissolving the silicone resin is absorbed on the substrate onto which it is applied, the silicone resin which remains on the substrate may also form a film.

The compositions of the present invention may comprise propylphenylsilsesquioxane resins, which have been disclosed in patent publications WO2005/090444, published on Sep. 29, 2005; US20040180011, published on Sep. 16, 2004; and US20040156806, published on Aug. 12, 2004.

The propylphenylsilsesquioxane resin comprises at least about 70 mole % of propyl siloxy units ($C_3H_7SiO_{3/2}$), based on the total mole % siloxy units of the resin, and at most about 30 mole % of phenyl siloxy units ($C_6H_5SiO_{3/2}$), based on the total mole % siloxy units of the resin.

The mole % of propyl siloxy units to phenyl siloxy units can be adjusted depending on an intended application. As such, it is possible to have propylphenylsilsesquioxane resins having a mole % propyl siloxy units:phenyl siloxy units ranging from about 70:30 to about 100:0, such as 70:30; 80:20; 90:10; and 100:0; and subranges therebetween. When the mole % of the propyl siloxy units is about 100 mole %, the propylphenylsilsesquioxane resin is referred to as a propylsilsesquioxane resin.

A suitable example of a propylphenylsilsesquioxane resin for use in cosmetic compositions of the present invention includes, but is not limited to, a propylsilsesquioxane resin commercially available from Dow-Corning under the tradename DC 670 Fluid.

The propylphenylsilsesquioxane film forming resin may be present in an amount ranging from about 0.5% to about 50% by weight, such as from about 1% to about 40% by weight, such as from about 2% to about 30% by weight, such as from about 3% to about 20% by weight, and such as from about 4% to about 10% by weight, all weights based on the weight of the composition as a whole.

Silicone Acrylate Copolymers

The composition of the present invention may contain silicone acrylate copolymers.

Silicone acrylate copolymers are another specific form of film forming silicone resins. They are available as silicone acrylate copolymers with a (meth)acrylate backbone grafted with a silicone chain or as a silicone backbone grafted with a (meth)acrylate, or as a silicone acrylate dendrimer.

Silicone acrylate dendrimers, such as those described and claimed in U.S. Pat. No. 6,280,748, the entire contents of which is hereby incorporated by reference, are preferred for use in the composition of the present invention. The silicone acrylate dendrimer is comprised of a vinyl polymer having a carbosiloxane dendrimer structure in its side molecular chain. It is characterized by a vinyl-type polymer which has in its side molecular chain a carbosiloxane dendrimer structure. The term "carbosiloxane dendrimer structure" is a structure with high-molecular-weight groups branched with high regularity in a radial direction from a single core.

The vinyl polymer backbone is formed from a vinyl-type monomer which contains a radical polymerizable vinyl group. In its broadest definition, there are no particular limitations with regards to the type of such a monomer. A particularly preferred vinyl polymer is a (meth)acrylate.

The number-average molecular weight of the silicone acrylate dendrimers for use in the composition of the present invention ranges from about 3,000 to about 2,000,000, such as from about 5,000 to about 800,000.

Particularly preferred silicone acrylate dendrimers for use in the composition of the present invention are available from Dow Corning as FA-4001 CM silicone acrylate, a 30% solution in cyclomethicone, and as FA-4002 ID silicone acrylate, a 40% solution in isododecane, under the INCI name of Acrylates/Polytrimethylsiloxymethacrylate Copolymer.

The silicone acrylate copolymer may be present in the composition of the invention in an amount ranging from about 0.5% to about 20% by weight, such as from about 0.7% to about 15% by weight, such as from about 1% to about 10% by weight, all weights based on the weight of the composition as a whole.

Pulverulent Phase

A composition of the invention may contain a pulverulent phase materials besides the microcapsules defined above.

A composition according to the invention may comprise at least 1% by weight and more particularly at least 5% by weight of pulverulent phase relative to the total weight of the said composition.

More particularly, a composition according to the invention may comprise at least 15% by weight and more particularly at least 20% by weight of pulverulent phase relative to the total weight of the said composition.

For the purposes of the present invention, this pulverulent phase may comprise, besides the microcapsules required according to the invention, at least one non-entrapped particulate material chosen from fillers; pigments; nacres; particles with a metallic tint; and mixtures thereof.

Thus, a composition according to the invention advantageously may comprise from 1% to 70% by weight, preferably from 5% to 60% by weight and better still from 10% to 50% by weight of pulverulent phase relative to the total weight of the said composition.

Thus, a composition according to the invention advantageously may comprise from 15% to 70% by weight, preferably from 20% to 60% by weight and better still from 25% to 50% by weight of pulverulent phase relative to the total weight of the said composition.

a) Non Entrapped Filler

For the purposes of the present invention, the term "fillers" should be understood as meaning colourless or white solid particles of any form, which are in an insoluble and dispersed form in the medium of the composition.

These fillers, of mineral or organic, natural or synthetic nature, give the composition containing them softness and give the makeup result a matt effect and uniformity.

A composition according to the invention may comprise from 0.5% to 50% by weight and preferably from 1% to 30% by weight of fillers relative to the total weight of the said composition.

This amount of fillers does not include the amount of hollow particles required in parallel according to the invention.

Among the mineral fillers that may be used in the compositions according to the invention, mention may be made of natural or synthetic mica, talc, kaolin, natural or synthetic sericite, silica, hydroxyapatite, boron nitride, calcium carbonate, hollow silica microspheres (Silica beads from Maprecos), glass or ceramic microcapsules; composites of silica and titanium dioxide, such as the TSG series sold by Nippon Sheet Glass, and mixtures thereof.

Among the organic fillers that may be used in the compositions according to the invention, mention may be made of polyamide powders (Nylon® Orgasol from Atochem), poly-β-alanine powder and polyethylene powder, polytetrafluoroethylene (Teflon®) powder, lauroyllysine, tetrafluoroethylene polymer powders, spherical powders of crosslinked elastomeric organopolysiloxane, described especially in document JP-A-02-243612, such as those sold under the name Trefil Powder E 2-506C or DC9506 or DC9701 by the company Dow Corning, silicone resins, which are products of hydrolysis and polycondensation of siloxane mixtures of formulae (R)3SiOHCH3 and Si(OCH3)4, R representing an alkyl group containing from 1 to 6 carbon atoms (for example KSP 100 from Shin-Etsu), silicone resin microbeads (for example Tospearl® from Toshiba), Polypore® L200 (Chemdal Corporation), polyurethane powders, in particular crosslinked polyurethane powders comprising a copolymer, the said copolymer comprising trimethylol hexyl lactone, for instance the polymer of hexamethylene diisocyanate/trimethylol hexyl lactone, sold under the name Plastic powder D-400® or Plastic Powder D-800® by the company Toshiki, and mixtures thereof.

Among the other organic fillers that may be used in the compositions according to the invention, mention may be made of starch-based or cellulose-based powders. Examples of such fillers that may be mentioned include the Dry Flo products sold by Akzo Nobel and the Cellubeads products sold by the company Daito Kasei.

Advantageously, the fillers in accordance with the invention are mineral fillers, preferably chosen from mica, sericite, kaolin, talc and silica, and mixtures thereof.

c) Non Entrapped Particulate Materials for Colouring Purposes.

These additional colouring particulate materials may be present in a proportion of from 0 to 40% by weight, preferably from 1% to 30% by weight or even 5% to 30% by weight relative to the total weight of the composition containing them.

They may especially be pigments, nacres and/or particles with metallic tint products, these materials possibly being surface-treated.

The term "pigments" should be understood as meaning white or coloured, mineral or organic particles that are insoluble in an aqueous solution, which are intended to colour and/or opacify the composition containing them.

A composition according to the invention may comprise from 0.01% to 40% by weight, preferably from 0.1% to 20% by weight and better still from 1% to 15% by weight of pigments relative to the total weight of said composition.

The pigments may be white or coloured, and mineral and/or organic.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

According to a specific embodiment, the composition of the invention contain at least non-entrapped inorganic pigments chosen from titanium dioxide, zinc oxide, cerium oxide, and/or fillers chosen from bismuth oxychloride or boron nitride, in order to improve the white color of the composition.

According to a specific embodiment, the compositions of the invention contain at least non-entrapped $TiO_2$.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term "nacres" should be understood as meaning iridescent or non-iridescent coloured particles of any shape, especially produced by certain molluscs in their shell or alternatively synthesized, which have a colour effect via optical interference.

A composition of the invention may comprise from 1% to 80% by weight, preferably from 5% to 60% by weight and better still from 10% to 40% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made of gold-coloured nacres sold especially by the company Engelhard under the name Brilliant gold 212G (Timica), Gold 222C (Cloisonne), Sparkle gold (Timica), Gold 4504 (Chromalite) and Monarch gold 233× (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nuantique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red-tinted nacres with a golden tint sold especially by the company Engelhard under the name Sunstone G012 (Gemtone); the pink nacres sold especially by the company Engelhard under the name Tan opale G005 (Gemtone); the black nacres with a golden tint sold especially by the company Engelhard under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

Advantageously, the nacres in accordance with the invention are micas coated with titanium dioxide or with iron oxide, and also bismuth oxychloride.

The term "particles with a metallic tint", within the meaning of the present invention, denotes particles whose nature, size, structure and surface state allow them to reflect the incident light, especially in a non-iridescent manner.

A composition according to the invention may comprise from 1% to 50% by weight and preferably from 1% to 20% by weight of particles with a metallic tint relative to the total weight of said composition.

Particles with a substantially flat outer surface are also suitable, since they can, if their size, structure and surface state allow it, more easily give rise to a strong specular reflection, which may then be termed a mirror effect.

The particles with a metallic tint that may be used in the invention may, for example, reflect light in all the components of the visible region without significantly absorbing one or more wavelengths. The spectral reflectance of these particles may, for example, be greater than 70% and better still at least 80%, or even 90% or 95%, in the range 400-700 nm.

These particles generally have a thickness of less than or equal to 1 μm, especially less than or equal to 0.7 μm and in particular less than or equal to 0.5 μm.

The particles with a metallic tint that may be used in the invention are in particular chosen from:
　particles of at least one metal and/or of at least one metal derivative,
　particles comprising a monomaterial or multimaterial organic or mineral substrate, at least partially coated with at least one layer with a metallic tint comprising at least one metal and/or at least one metal derivative, and mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

Among the metal derivatives that may be present in said particles, mention may be made especially of metal oxides, for instance titanium oxide, especially $TiO_2$, iron oxide, especially $Fe_2O_3$, tin oxide, chromium oxide, barium sulfate and the following compounds: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

Illustrations of these particles that may be mentioned include aluminum particles, such as those sold under the names Starbrite 1200 EAC® by the company Siberline and Metalure® by the company Eckart.

Mention may also be made of metal powders of copper or of alloy mixtures such as the references 2844 sold by the company Radium Bronze, metallic pigments, for instance aluminum or bronze, such as those sold under the names Rotosafe 700 from the company Eckart, silica-coated aluminum particles sold under the name Visionaire Bright Silver from the company Eckart, and metal alloy particles, for instance the silica-coated bronze (alloy of copper and zinc) powders sold under the name Visionaire Bright Natural Gold from the company Eckart.

As illustrations of particles of this second type, mention may be made more particularly of:

Glass particles coated with a metallic layer, especially those described in documents JP-A-09188830, JP-A-10158450, JP-A-10158541, JP-A-07258460 and JP-A-05017710.

As illustrations of these particles comprising a glass substrate, mention may be made of those coated, respectively, with silver, gold or titanium, in the form of platelets, sold by the company Nippon Sheet Glass under the name Microglass Metashine. Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company. Those coated either with brown iron oxide or with titanium oxide, tin oxide or a mixture thereof, for instance those sold under the name Reflecks by the company Engelhard or those sold under the name Metashine MC 2080GP by the company Nippon Sheet Glass.

These metal-coated glass particles may be coated with silica, for instance those sold under the name Metashine series PSS1 or GPS1 by the company Nippon Sheet Glass.

Particles comprising a spherical glass substrate optionally coated with a metal, especially those sold under the name Prizmalite Microsphere by the company Prizmalite Industries.

Pigments of the Metashine 1080R range sold by the company Nippon Sheet Glass Co. Ltd are also suitable for the invention. These pigments, more particularly described in patent application JP 2001-11340, are C-Glass glass flakes comprising 65% to 72% $SiO_2$, coated with a layer of titanium oxide of rutile type ($TiO_2$). These glass flakes have a mean thickness of 1 micron and a mean size of 80 microns, i.e. a mean size/mean thickness ratio of 80. They have blue, green or yellow tints or a silver shade depending on the thickness of the $TiO_2$ layer.

Particles comprising a silver-coated borosilicate substrate, are also known as "white nacres".

Particles comprising a metal substrate such as aluminum, copper or bronze, in the form of platelets, are sold under the trade name Starbrite by the company Silberline and under the name Visionaire by the company Eckart.

Particles comprising a synthetic mica substrate coated with titanium dioxide, and for example particles with a size of between 80 and 100 μm, comprising a synthetic mica (fluorophlogopite) substrate coated with titanium dioxide representing 12% of the total weight of the particle, sold under the name Prominence by the company Nihon Koken.

The particles with a metallic tint may also be chosen from particles formed from a stack of at least two layers with different refractive indices. These layers may be of polymeric or metallic nature and may especially include at least one polymer layer.

Thus, the particles with a metallic effect may be particles derived from a multilayer polymer film.

The choice of materials intended to constitute the various layers of the multilayer structure is obviously made so as to give the particles thus formed the desired metallic effect.

Such particles are especially described in WO 99/36477, U.S. Pat. No. 6,299,979 and U.S. Pat. No. 6,387,498 and more particularly identified below in the goniochromatic section.

Advantageously, the particles with a metallic tint in accordance with the invention are particles with a spherical or non-spherical glass substrate, and also particles with a metallic substrate.

According to a specific embodiment, a composition according to the invention contains at least reflective particles in particular selected the nacres, particles with a metallic tint, and bismuth oxichloride and their mixtures.

As illustrations of particles of this second type, mention may be made more particularly of:

Particles comprising a synthetic mica substrate coated with titanium dioxide coated or particles comprising a spherical glass substrate optionally coated with either with brown iron oxide or with titanium oxide, tin oxide or a mixture thereof, for instance those sold under the name Reflecks by the company Engelhard or those sold under the name Metashine MC 2080GP by the company Nippon Sheet Glass. Such particles are detailed in JP-A-09188830, JP-A-10158450, JP-A-10158541, JP-A-07258460 and JP-A-05017710.

Particles with metallic effect comprising mineral substrate coated with a metal. It may be a particles having a silver-coated borosilicate substrate, are also known as "white nacres.

Particles comprising a spherical glass substrate coated with silver, especially those sold under the name MICROGLASS METASHINE REFSX 2025 PS by TOYAL. Particles comprising a spherical glass substrate coated with nickel/chrome/molybdene alloy especially those sold under the name CRYSTAL STAR GF 550, GF 2525 by the same company.

Particles having metallic effect and having on surface a metallic compound optionally coated particles sold under the names METASHINE® LE 2040 PS, METASHINE® 5 MC5090 PS or METASHINE® MC280GP (2523) by the company NIPPON SHEET GLASS, SPHERICAL SILVER POWDER® DC 100, SILVER FLAKE® JV 6 or GOLD POWDER® A1570 by the company ENGELHARD, STARLIGHT REFLECTIONS FXM® by the company ENERGY STRATEGY ASSOCIATES INC, BRIGHT SILVER® 1 E 0.008×0.008 by the company MEADOWBROOK INVENTIONS, ULTRAMIN® (ALUMINUM POUDRE FINE LIVING), and COSMETIC METALLIC POWDER VISIONAIRE BRIGHT SILVER SEA®, COSMETIC METALLIC POWDER VISIONAIRE NATURAL GOLD® (60314) or COSMETIC METALLIC POWDER VISIONAIRE HONEY® 560316° by the company ECKART.

More preferably, these reflective particles are chosen in the group consisting of bismuth oxichloride particles, mica particles coated with titanium oxide, and mixtures thereof.

According to a specific embodiment, a composition of the invention contains at least bismuth oxichloride (CI 77163).

Advantageously, a composition of the invention may also contains at least nacres comprising a silver-coated borosilicate substrate, are also known as "white nacres". Such particles are sold by the firm MERCK under the tradename Xirona Silver.

The composition may comprise reflective particles pre-dispersed in one oil selected from mineral, vegetable oils and ester oils.

According to a preferred embodiment, these reflective particles are present in the compositions of the invention under a pre-dispersed form in at least one oil selected in the group consisting of Mineral oils
Vegetable oils like sweet almond oil, wheat germ oil, jojoba oil, apricot oil, soybean oil, canola oil, castor oil;
Esters such as octyl dodecanol, octyldodecyl neopentanoate, caprylic/capric triglycerides, pentaerythrityl tetraisostearate, isodecyl neopentanoate, diisopropyl sebacate, $C_{12}$-$C_{15}$ alkyl benzoate, ethylhexyl ethylhexanoate, ethylhexyl hydroxystearate,
and mixture thereof.

More preferably, the oil is chosen in the group consisting of ethyl (2) hexyl hydroxystearate, or castor oil, and preferably ethyl (2) hexyl hydroxystearate.

Thus, according to a specific and preferred embodiment, a composition of the invention comprises, in a physiologically acceptable medium,
(i) at least microcapsules of the invention and
(ii) at least reflective particles under a pre-dispersed form in at least one oil selected in the group consisting of ethyl (2) hexyl hydroxystearate or castor oil and preferably ethyl (2) hexyl hydroxystearate.

Advantageously, the reflective particles are chosen among bismuth oxichloride particles and mica particles covered with titanium oxide, said particles being pre-dispersed ethyl (2) hexylhydroxystearate.

According to a specific embodiment, the composition of the invention comprises a pre-dispersion comprising from 68% to 72% by weight of bismuth oxichloride in 28% to 32% by weight of ethyl (2) hexylhydroxystearate, with respect to the total weight of the pre-dispersion i.e a weight ratio bismuth oxichloride/oil(s) greater or equal to 2, and preferably ranging from 2 to 2.6.

Such a dispersion is sold by the firm MERCK under the tradename Xirona Silver Biron® Liquid Silver.

Additional Moisturizers

For a particular care application, a composition according to the invention may comprise at least one additional moisturizer (also known as a humectant).

The moisturizer(s) may be present in the composition in a content ranging from 0.1% to 15% by weight, especially from 0.5% to 10% by weight or even from 1% to 6% by weight, relative to the total weight of the said composition.

Polyhydric alcohols, preferably of $C_2$-$C_8$ and more preferably $C_3$-$C_6$, preferably such as glycerol, propylene glycol, 1,3-butylene glycol, pentylene glycol, hexylene glycol, dipropylene glycol, diethylene glycol and diglycerol, and mixtures thereof, glycerol and derivatives thereof are known as moisturizers or humectants.

The composition according to the invention may also comprise an additional moisturizers or humectants.

These additional moisturizers or humectants that may especially be mentioned include sorbitol, glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, urea and derivatives thereof, especially Hydrovance (2-hydroxyethylurea) sold by National Starch, lactic acids, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* sold under the name Moist 24 by the company Sederma, acrylic acid homopolymers, for instance Lipidure-HM® from NOF Corporation, beta-glucan and in particular sodium carboxymethyl beta-glucan from Mibelle-AG-Biochemistry; a mixture of passionflower oil, apricot oil, corn oil and rice bran oil sold by Nestle under the name Nutra-Lipids®; a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by Chimex under the trade name Mexoryl SBB®; an oil of musk rose sold by Nestle; spheres of collagen and of chondroitin sulfate of marine origin (Atelocollagen) sold by the company Engelhard Lyon under the name Marine Filling Spheres; hyaluronic acid spheres such as those sold by the company Engelhard Lyon; arginine, argan oil, and mixtures thereof.

Preferably, use will be made of a moisturizer chosen from glycerol, urea and derivatives thereof, especially Hydrovance® sold by National Starch, a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by Chimex under the trade name Mexoryl SBB®; argan oil, and mixtures thereof.

More preferably, glycerol will be used.

Sunscreen/Sunblock Agents

Sunscreens are important skin-care products used to prevent photoaging and skin cancer. There are two groups of sunscreens: UVA sunscreens, which block UV radiation in the wavelength range of about 320 to 400 nm, and UVB sunscreens, which block radiation in the range of 290 to 320 nm.

The compositions in accordance with the invention comprise organic and/or inorganic UV sunscreen ingredients active in the UV-A and/or UV-B region which are hydrophilic and/or lipophilic.

In particular, the UV sunscreen ingredients according to the invention might have a solubility parameter ranging from 8.0 to 9.5. Said UV sunscreen ingredients have a good plasticizer function.

Advantageously, the UV sunscreen agent according to the invention might have a molecular weight ranging from 150 to 500 g/mol and contain hydrophobic sites and benzene nucleus or electron resonance group binding with polar sites.

The hydrophilic and/or lipophilic organic UV sunscreen ingredients are selected in particular from benzylidene camphor derivatives, dibenzoylmethane derivatives; cinnamic derivatives; salicylic derivatives; benzophenone derivatives; β,β-diphenylacrylate derivatives; p-aminobenzoic acid (PABA) derivatives; and their mixtures.

Mention may be made, as examples of organic UV sunscreen ingredients, of those denoted below under their INCI names:

para-Aminobenzoic acid derivatives:
PABA,
Ethyl PABA,
Ethyl Dihydroxypropyl PABA,
Ethylhexyl Dimethyl PABA, marketed in particular under the trademark "Escalol 507" by ISP,
Glyceryl PABA,
Dibenzoylmethane Derivatives:
Butyl Methoxydibenzoylmethane, marketed in particular under the trademark "Parsol 1789" by Hoffmann-La-Roche,
Isopropyl Dibenzoylmethane,
Salicylic Derivatives:
Homosalate, marketed under the trademark "Eusolex HMS" by Rona/EM Industries,
Ethylhexyl Salicylate, marketed under the trademark "Neo Heliopan OS" by Haarmann and Reimer,
Dipropyleneglycol Salicylate, marketed under the trademark "Dipsal" by Scher,
TEA Salicylate, marketed under the trademark "Neo Heliopan TS" by Haarmann and Reimer,
Cinnamic Derivatives:
Ethylhexyl Methoxycinnamate, marketed in particular under the trademark "Parsol MCX" by Hoffmann-LaRoche,
Isopropyl Methoxycinnamate,
Isoamyl Methoxycinnamate, marketed under the trademark "Neo Heliopan E 1000" by Haarmann and Reimer,
Cinoxate,
DEA Methoxycinnamate,
Diisopropyl Methylcinnamate,
Glyceryl Ethylhexanoate Dimethoxycinnamate,
β,β-Diphenylacrylate Derivatives:
Octocrylene, marketed in particular under the trademark "Uvinul N539" by BASF,
Etocrylene, marketed in particular under the trademark "Uvinul N35" by BASF,
Benzophenone Derivatives:
Benzophenone-1, marketed under the trademark "Uvinul 400" by BASF,
Benzophenone-2, marketed under the trademark "Uvinul D50" by BASF,
Benzophenone-3 or Oxybenzone, marketed under the trademark "Uvinul M40" by BASF,
Benzophenone-4, marketed under the trademark "Uvinul MS40" by BASF,
Benzophenone-5,
Benzophenone-6, marketed under the trademark "Helisorb 11" by Norquay,
Benzylidene camphor derivatives:
Terephthalylidene dicamphor sulfonic acid,
4-Methylbenzylidene camphor
and their mixtures.

The organic UV filter is selected from an aminobenzoic acid derivative, a dibenzoylmethane derivative, a salicylic acid derivative, a cinnamic derivative, a β,β diphenylacrylate derivative, a benzophenone derivative, benzylidene camphor derivative, and mixtures thereof.

The preferred UV sunscreen ingredients are selected in the group consisting of cinnamic derivatives, β,β diphenylacrylates derivatives, salicylic derivatives, and their mixtures.

The preferred UV sunscreen ingredients are especially selected in the group consisting of ethylhexyl methoxycinnamate, octocrylene and ethylhexyl salicylate, and their mixtures.

Mention may be made especially of ethylhexyl methoxycinnamate sold under the tradename UVINUL MC 80® by the company BASF, of ethylhexyl salicylate sold under the tradename NEO HELIOPAN OS® by the company SYMRISE and of octocrylene sold under the tradename NEO HELIOPAN 303® by the company SYMRISE.

The composition in accordance with the invention may comprise from 0.1% to 30% by weight, for example from 0.5 to 20% by weight, for example from 1 to 15% by weight, and for example at least 1% by weight, of UV sunscreen ingredient relative to the total weight of the composition.

According to one exemplary embodiment, the composition may comprise the microcapsules and at least one UV sunscreen ingredient in a weight ratio [mineral filler/UV sunscreen ingredient] ranging from 0.20 to 10, for example from 1 to 9.5, preferably from 3 to 9.

Advantageously, the composition of the invention comprises at least one UV filter and eventually an active agent.

Active Agents

For application in particular for caring for or making up skin, the composition according to the invention may comprise at least one active agent chosen from:

According to one advantageous embodiment, the combination according to the invention may be combined with one or more supplementary cosmetic active agents.

These active agents may be chosen from antiwrinkle agents vitamins, in particular B3, B8, B12 and B9, moisturizers, desquamating agents, anti-ageing active agents, depigmenting agents, antioxidants, etc.

These active agents may be present in the composition in a content ranging from 0.001% to 20% by weight, preferably from 0.01% to 10% by weight, and more preferably from 0.01% to 5% by weight, relative to the total weight of the composition.

Antiwrinkle agents: mention may be made to ascorbic acid and derivatives thereof, such as magnesium ascorbyl phosphate and ascorbyl glucoside; tocopherol and derivatives thereof, such as tocopheryl acetate; nicotinic acid and precursors thereof, such as nicotinamide; ubiquinone; glutathione and precursors thereof, such as L-2-oxothiazolidine-4-carboxylic acid; C-glycoside compounds and derivatives thereof, as described in particular hereinafter: extracts of plants, and in particular extracts of sea fennel and of olive leaf; and also plant proteins and hydrolysates thereof, such as rice or soybean protein hydrolysates; algal extracts and in particular of laminaria; bacterial extracts; sapogenins, such as diosgenin and extracts of Dioscorea plants, in particular of wild yam, containing them; α-hydroxy acids; β-hydroxy acids, such as salicylic acid and 5-n-octanoylsalicylic acid; oligopeptides and pseudodipeptides and acyl derivatives thereof, in particular {2-[acetyl-(3-trifluoromethylphenyl) amino]-3-methylbutyryl amino}acetic acid and the lipopeptides sold by the company Sederma under the trade names Matrixyl 500 and Matrixyl 3000; lycopene; manganese salts and magnesium salts, in particular manganese and magnesium gluconates; and mixtures thereof;

Desquamating agents: mention will be made of beta-hydroxy acids, in particular salicylic acids and derivatives thereof other than 5-n-octanoylsalicylic acid; urea; glycolic acid, citric acid, lactic acid, tartaric acid, malic acid or mandelic acid; 4-(2-hydroxyethyl)piperazine-1-propanesulphonic acid (HEPES); extract of Saphora japonica; honey; N-acetylglucosamine; sodium methylglycine diacetate, alpha-hydroxy acids (AHAs), beta-hydroxy acids (BHAs), and mixtures thereof;

Depigmenting agents: mention may be made of ceramides, vitamin C and derivatives thereof, in particular vitamin CG, CP and 3-0 ethyl vitamin C, alpha- and beta-arbutin, ferulic acid, kojic acid, resorcinol and derivatives thereof, calcium D-pantetheine sulphonate, lipoic acid, ellagic acid, vitamin B3, phenylethyl resorcinol, for instance Symwhite 377® from the company Symrise, a kiwi fruit (*Actinidia chinensis*) juice sold by Gattefosse, an extract of *Paeonia suffructicosa* root, such as the product sold by the company Ichimaru Pharcos under the name Botanpi Liquid B®, an extract of brown sugar (*Saccharum officinarum*), such as the extract of molasses sold by the company Taiyo Kagaku under the name Molasses Liquid, a mixture of undecylenic acid and undecylenoyl phenyl alanine, such as Sepiwhite MSH® from Seppic;

Antioxidants: mention may more particularly be made of tocopherol and esters thereof, in particular tocopheryl acetate; EDTA, ascorbic acid and derivatives thereof, in particular magnesium ascorbyl phosphate and ascorbyl glucoside; chelating agents, such as BHT, BHA, N,N'-bis(3,4,5-trimethoxybenzyl)ethylenediamine and its salts, and mixtures thereof.

When the active principle ascorbyl glucoside is present in the cosmetic composition according to the present invention, it is present in an amount lower than 0.05% by weight, and more preferably of 0.01% by weight relative to the total weight of the composition.

Galenic Formulation

A composition according to the invention may be in the form of makeup compositions and/or care compositions for keratin materials, in particular for skin or lips. Particularly, a composition according to the invention may be a BB product or a foundation especially to be applied on the face or neck, a product for masking dark circles, a concealer product, a tinted cream, a colored composition for care or for making up the skin, especially for the face or body or an after-sun composition.

In a preferred embodiment, a composition according to the present invention is a non-rinsing composition: the composition is not intended to be rinsed after application on the skin.

In another preferred embodiment, the composition according to the present invention is not contained in a dispenser comprising a pump. This is advantageous since it avoids the risk for the microcapsules to be broken. Indeed, when using such a dispenser, said microcapsules could be crushed before their application on the keratin materials.

It is understood that the compositions according to the invention can be in any galenical form conventionally used for topical application, especially in the form of liquid or semi-liquid consistency of the milk type, or of soft, semi-solid or solid consistency of the cream or gel type, or alternatively, an emulsion obtained by dispersing a fatty phase in an aqueous phase (O/W), an emulsion obtained by dispersing an aqueous phase in a fatty phase in (W/O), a multiple emulsion (W/O/W, O/W/O), or a foam.

Particularly the composition is in the form selected from the group consisting in a gel and in particular a transparent gel, a water-in-oil emulsion, an oil-in-water emulsion and a foam.

Surfactants

A composition according to the invention may comprise at least one surfactant (emulsifier), chosen especially from amphoteric, anionic, cationic and nonionic surfactants, used alone or as a mixture.

The surfactants are generally present in the composition in a proportion that may range, for example, from 0.3% to 20% by weight, in particular from 0.5% to 15% by weight and more particularly from 1% to 10% by weight of surfactants relative to the total weight of the composition.

Needless to say, the surfactant is chosen so as to effectively stabilize the emulsions more particularly under consideration according to the invention, namely of O/W, W/O or O/W/O type. This choice falls within the competence of a person skilled in the art.

For example, when the emulsifier potassium cetyl phosphate is present in the cosmetic composition according to the present invention, it is in a proportion that may range, for example, from 0.2% to 3% by weight, more particularly from 0.5% to 1.5% by weight and more preferably from 0.8% to 1.2% by weight, and even more preferably 1% by weight relative to the total weight of the composition.

O/W Emulsifiers

Examples that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

Glyceryl esters of fatty acids that may especially be mentioned include glyceryl stearate (glyceryl monostearate, distearate and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Fatty acid esters of glucose or of alkylglucose that may be mentioned in particular include glucose palmitate, alkylglucose sesquistearates, for instance methylglucose sesquistearate, alkylglucose palmitates, for instance methylglucose palmitate or ethylglucose palmitate, fatty esters of methylglucoside and more especially the diester of methylglucoside and of oleic acid (CTFA name: methyl glucose dioleate); the mixed ester of methylglucoside and of the oleic acid/hydroxystearic acid mixture (CTFA name: methyl glucose dioleate/hydroxysterate); the ester of methylglucoside and of isostearic acid (CTFA name: methyl glucose isostearate); the ester of methylglucoside and of lauric acid (CTFA name: methyl glucose laurate); the mixture of the monoester and diester of methylglucoside and of isostearic acid (CTFA name: methyl glucose sesquiisostearate); the mixture of the monoester and diester of methylglucoside and of stearic acid (CTFA name: methyl glucose sesquistearate) and in particular the product sold under the name Glucate SS by the company Amerchol, and mixtures thereof.

Examples of oxyethylenated ethers of a fatty acid and of glucose or of alkylglucose that may be mentioned include the oxyethylenated ethers of a fatty acid and of methylglucose, and in particular the polyethylene glycol ether of the diester of methyl glucose and of stearic acid containing about 20 mol of ethylene oxide (CTFA name: PEG-20 methyl glucose distearate), such as the product sold under the name Glucam E-20 distearate by the company Amerchol; the polyethylene glycol ether of the mixture of monoester and diester of methylglucoside and of stearic acid containing about 20 mol of ethylene oxide (CTFA name: PEG-20 methyl glucose sesquistearate) and in particular the product sold under the name Glucamate SSE-20 by the company Amerchol, and the product sold under the name Grillocose PSE-20 by the company Goldschmidt, and mixtures thereof.

Examples of sucrose esters that may be mentioned include sucrose palmitostearate, sucrose stearate and sucrose monolaurate.

Examples of fatty alcohol ethers that may be mentioned include polyethylene glycol ethers of fatty alcohols containing from 8 to 30 carbon atoms and especially from 10 to 22 carbon atoms, such as polyethylene glycol ethers of cetyl alcohol, of stearyl alcohol or of cetearyl alcohol (mixture of cetyl alcohol and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof.

Sugar ethers that may especially be mentioned are alkylpolyglucosides, for example decylglucoside, for instance the product sold under the name Mydol 10 by the company Kao Chemicals, the product sold under the name Plantaren 2000 by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; cocoglucoside, for instance the product sold under the name Plantacare 818/UP by the company Henkel; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl alcohol and behenyl alcohol and arachidyl glucoside, sold under the name Montanov 202 by the company SEPPIC; cocoylethylglucoside, for example in the form of the mixture (35/65) with cetyl alcohol and stearyl alcohol, sold under the name Montanov 82 by the company SEPPIC; and mixtures thereof.

W/O Emulsifiers

For the W/O emulsions, hydrocarbon-based or silicone surfactants may be used.

According to one embodiment variant, hydrocarbon-based surfactants are preferred.

Examples of hydrocarbon-based surfactants that may be mentioned include polyester polyols, for instance PEG-30 dipolyhydroxystearate sold under the reference Arlacel P 135 by the company Uniqema, and polyglyceryl-2 dipolyhydroxystearate sold under the reference Dehymuls PGPH by the company Cognis.

Examples of silicone surfactants that may be mentioned include alkyl dimethicone copolyols such as lauryl methicone copolyol sold under the name Dow Corning 5200 Formulation Aid by the company Dow Corning and cetyl dimethicone copolyol sold under the name Abil EM 90 by the company Goldschmidt, or the polyglyceryl-4 isostearate/cetyl dimethicone copolyol/hexyl laurate mixture sold under the name Abil WE 09 by the company Goldschmidt.

One or more co-emulsifiers may also be added thereto. The co-emulsifier may be chosen advantageously from the group comprising polyol alkyl esters. Polyol alkyl esters that may especially be mentioned include glycerol and/or sorbitan esters, for example the polyglyceryl-3 diisostearate sold under the name Lameform TGI by the company Cognis, polyglyceryl-4 isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

These compositions are prepared according to the usual methods.

The compositions of this type may be in the form of a facial and/or body care or makeup product, and may be conditioned, for example, in the form of cream in a jar or of fluid in a tube.

The compositions according to the invention may be solid or more or less fluid and having the appearance of a cream, a gel particularly a transparent gel, an ointment, a milk, a lotion, a serum, a paste, a foam (with or without associated propellant), a stick.

According to an embodiment, the composition is in the form of a gel and in particular a transparent gel, and comprising from 1 to 10% by weight relative to the weight of the composition of microcapsules.

The composition according to the invention may also be in the form of a gel and in particular a transparent or translucent gel, this composition comprises one or more hydrophilic gelifying agents and from 1 to 10%, preferably from 1 to 5% by weight relative to the weight of the composition of microcapsules.

Preferably, the viscosity of the gel according to the invention is superior or equal to 20 UD (Mobile 3) by Rheomat at 25° C.

The viscosity is generally measured at 25° C. with a viscosimeter RHEOMAT RM 180 with Mobile 3 adapted to the viscosity of the product to be tested (mobile is chosen for having a measure between 10 and 90 for UD Unit Deviation), the measure being made after 10 nm rotating the mobile inside the composition, with a cisaillement from 200 s−1. The UD values may then be converted in Poises (1 Poise=0.1 Pa·s) with a correspondence table.

More preferably, the composition contains a gelified aqueous phase.

Hydrophilic gelling agents (also called hydrophilic gelifying agent) that may be mentioned in particular include those listed above.

More preferably the aqueous gel is transparent.

The expression "transparent aqueous medium" means a medium allowing light to pass without causing deviation by refraction or reflection. The transparency of the aqueous medium can be measured using a turbidimeter. The portable Turbidimeter 2100P® Model from HACH company may be used, for example, for measuring the ranges of transparency of the composition. The composition is considered to be transparent when the measured value of turbidity is between 0 and 250 NTU and is considered as a translucent for a value of turbidity from 250 to 1000 NTU.

The transparent compositions, when placed in front of a 0.01 m thick black line with diameter of 2 mm drawn on a white sheet, reveal this black line, as opposed to an opaque composition that is to say, not transparent which would not allow it.

The changing color composition in the form of a transparent gel according to the invention preferably comprises water and multi-layered microcapsules containing releasable colorant(s).

In a first preferred embodiment, a transparent gel according to the invention comprises at least one hydrophilic or lipophilic gelling agent and at least one water soluble emollient(s) and/or lipid(s) with a polar moiety.

In a first preferred embodiment, a transparent gel according to the invention comprises at least two types of different multi-layered microcapsules containing releasable colorant(s).

A transparent gel according to the invention, which is preferably a BB product or a foundation, provides very strong moisturizing sensation, transparent, cleaning bulk appearance with very comfortable feeling during application and sheer natural make-up result after application. These features help to deliver both skincare efficacy perception (watery, moisturization and transparent) as well as make-up efficacy (proper coverage).

Advantageously, a transparent gel contains a swelling agent, this agent allows a better swelling of the microcapsules thus rendering the microcapsules easier to break during application. Water, alcohols, glycols polyols may be used as swelling agent. Examples of swelling agents are disclosed above.

The moisturization may further be enhanced by introduction of one or more water soluble emollient(s) and/or lipid(s) with a polar moiety. PEG modified silane and silicone such as Bis-PEG-18 Methyl ether dimethyl silane, and/or PEG modified ester such as PEG-7 Olivate, PEG-7 Glyceryl Cocoate, PEG-30 Glyceryl Cocoate, PEG-80 Glyceryl Cocoate, may be used to enhance moisturization.

A solubilizer may also be added in order to keep the properties of the transparent gel on storage, in particular to make emollients solubilized in water phase, to make and keep gel transparent and stable in shelf lives. Polysorbate 20, PEG-60 hydrogenated castor oil may be mentioned as examples of solubilizers.

A transparent gel according to the invention presents a very beautiful, clean and tidy appearance, with pigments releasing during application without any particle feeling. Makeup results are perfectly and evenly provided after application.

A preferred embodiment of a transparent gel according to the invention comprises:

at least one of the polymers chosen from Acrylates/C10-30 Alkyl Acrylate Crosspolymer such as Permulen TR-1, Permulen TR-2, Carbopol 1382, Carbopol ETD 2020, preferably in a concentration from 0 to 10% wgt, more preferably from 0 to 2% wgt, Carbomer such as Synthalen K, carbopol 980 preferably in a concentration from 0 to 10% wgt, more preferably from 0 to 2% wgt, Ammonium acryloyldimethyl Taurate/Steareth-8 Methacrylate copolymer such as Aristoflex SNC, preferably in a concentration from 0 to 10% wgt, more preferably from 0 to 2% wgt, Acrylates copolymer such as Carbopol Aqua SF-1 preferably in a concentration from 0 to 10% wgt, more preferably from 0 to 2% wgt, Ammonium acryloyldimethyl taurate/steareth-25 Methacrylate Crosspolymer such as Aristoflex HMS, preferably in a concentration from 0 to 10% wgt, more preferably from 0 to 2% wgt, Ammonium acryloyldimethyl taurate such as Arisfoflex AVC, preferably in a concentration from 0 to 10% wgt, more preferably from 0 to 4% wgt and xanthan gum such as Keltrol CG, preferably in a concentration from 0 to 10% wgt, more preferably from 0 to 4% wgt.

Moreover, a transparent gel may contain at least one of the following swelling agent, water such as deionized water, preferably in a concentration from 0 to 90% wgt, more preferably from 30 to 70% wgt, alcohols preferably in a concentration from 0 to 50% wgt, more preferably from 1 to 20% wgt, glycols such as propyl glycol, butyl glycol, preferably in a concentration from 0 to 50% wgt, more preferably from 1 to 15% wgt, polyols such as glycerin, tetraols, preferably in a concentration from 0 to 50% wgt, more preferably from 1 to 10% wgt.

In addition, a transparent gel may contain at least one water soluble emollients chosen from Bis-PEG-18 Methyl ether dimethyl silane, PEG-7 Olivate, PEG-7 Glyceryl Cocoate, PEG-30 Glyceryl Cocoate, PEG-80 Glyceryl Cocoate, in a concentration from 0 to 20% wgt, more preferably from 0 to 5% wgt, and at least one solubilizers such as polysorbate 20, PEG-60 hydrogenated castor oil, in a concentration from 0 to 10% wgt, more preferably from 1 to 5% wgt.

Microcapsules such as Magic 60-WP0105, and Magic50-BW0105 from Korea Particle Technology in a concentration from 0.1 to 30% wgt, more preferably from 1 to 10% wgt may be introduced at last step with gentle stirring but without side scrapper after gel is made.

In the case of caring composition, the composition according to the invention comprises from 0.1% to 5% by weight and preferably from 0.1% to 3% by weight of microcapsules relative to the total weight of the said composition.

Such obtained transparent gel with microcapsules present a pure and clean appearance, with perfect stability under −20/20° C. (5 cycles), room temperature (25° C., 2 months), 37° C. (2 months) and 45° C. (2 months). The microcapsules release pigments during application without any particle feeling. Makeup results are perfectly and evenly provided after application.

A transparent gel could also by slightly colored.

In this case, a transparent gel comprises at least one non-entrapped colorant, preferably in an amount of less than 1% by weight based on the total weight of the total composition.

The composition may also be in a form of an gelly cream, or emulsionated gel, comprising oils and surfactants.

According to another embodiment, the changing color composition according to the invention is in the form of a foam comprising from 1 to 30% by weight relative to the weight of the composition of microcapsules.

The term "composition in (the) foam form" and the term "foam type formulation" have the same meaning and are understood to mean a composition comprising a gas phase (for example air) in the form of bubbles; another equivalent term is "composition expanded in volume".

In one embodiment, a foam composition is obtained without any propellant (non aerosol foam).

In another preferred embodiment, a foam composition is obtained with a propellant (aerosol foam)

The composition in the foam form according to the invention may be obtained from a composition of the invention used as "base composition" packaged in a product. This product may contain, besides the base composition, a propellant.

Thus, the present invention further relates to a product comprising:
a. a container defining at least one compartment;
b. a composition of the invention contained in said compartment,
c. a propellant to pressurize said composition inside said compartment; and
d. a dispensing head having an opening to be selectively put in fluid communication with said compartment in order to deliver said pressurized composition in the form of a foam.

According to yet another embodiment, the present invention relates to a kit comprising one of the product defined above and an applicator.

The compositions in the foam form according to the invention are formed stably in the form of mousse using a composition of the invention and air or an inert gas.

The air or the inert gas may represent especially from 10% to 500% and preferably from 20% to 200%, for example from 30% to 100% of the volume of the composition in the foam form.

This volume may be calculated by comparing the density of the base composition and of the in the foam form composition.

Besides air, gases that allow the composition in the foam form to be obtained are in particular inert gases, for example nitrogen, carbon dioxide, nitrogen oxides, noble gases or a mixture of the said gases. When the composition comprises an oxidation-sensitive compound, it is preferable to use an oxygen-free gas such as nitrogen or carbon dioxide.

The amount of gas introduced into the base composition contributes towards adjusting the density of the composition in the foam form to the desired value, for example less than or equal to 0.12 g/cm$^3$.

The composition in the foam form of the invention may have for example a density of less than or equal to 0.12 g/cm$^3$, for example ranging from 0.02 to 0.11 g/cm$^3$ and preferably from 0.06 to 0.10 g/cm$^3$, this density being measured at a temperature of about 20° C. and at atmospheric pressure according to the following protocol.

Density Measurement

The test is performed on 50 ml of composition introduced into a 50 ml polished Plexiglas® goblet ($V_1$) defining a cylindrical filling space 30 mm high having a base with a diameter of 46 mm. The goblet has a bottom wall 10 mm thick and a side wall 12 mm thick.

Before measurement, the composition to be characterized and the goblet are maintained at a temperature of about 20° C. The goblet is tared and the weight value ($M_1$) is recorded. The composition in the foam form is then introduced into the goblet so as to occupy the total volume, while avoiding the formation of air bubbles during the filling of the goblet. The assembly is left to stand for 10 seconds to allow the mousse to expand fully. The top of the goblet is then skimmed before weighing ($M_2$). The density is assessed according to the convention $\rho=(M_2-M_1)/50$.

Stability Measurement

The composition in the foam form according to the invention shows satisfactory stability, which may be calculated by measuring the volume of mousse ($V_2$) remaining in the goblet after 10 minutes according to the protocol described above for the density measurement.

The ratio $V_2/V_1$ corresponds to the ratio between the volume of the composition in the foam form after 10 minutes and the volume of the composition in the foam form after 10 seconds.

The expression "satisfactory stability" applies especially to compositions in the foam form with a ratio $$\frac{V_2}{V_1}$$

of greater than 0.85 and especially greater than 0.90, for example greater than 0.95.

For a given weight of composition in the foam form, the volume of the composition in the foam form is inversely proportional to the density of the composition in the foam form. Thus, the ratio between the density of the composition in the foam form measured after 10 seconds and the density of the composition in the foam form measured after 10 minutes may be greater than 0.85 and especially greater than 0.90, for example greater than 0.95.

Within the composition in the foam form according to the invention, the air pause may advantageously have a number-average size ranging from 20 µm to 500 µm and preferably ranging from 100 µm to 300 µm.

The composition in the foam form may be obtained from a composition of the invention in a distributor. This distributor may be an aerosol containing, besides the base composition, a propellant.

This propellant may represent less than 20% by weight of the base composition and in particular may represent from 1% to 10% by weight, for example from 2 to 8% by weight, for example at least 5% by weight of the total weight of the base composition. The propellant that may be used may be chosen from carbon dioxide, nitrogen, nitrous oxide and volatile hydrocarbons such as butane, isobutane, propane, ethane, pentane, isododecane or isohexadecane, and mixtures thereof.

It may especially be a propane/butane mixture (Liquified Petroleum Gas or LPG) in a weight ratio [propane/butane] ranging from 0.1 to 1, especially of 0.31.

The pressure of the propellant, and for example of said propane/butane mixture, in the aerosol may range from 0.20 to 0.50 MPa, for example from 0.20 to 0.40, and especially from 0.25 to 0.35 MPa.

The compositions in the foam form employed in the invention can be prepared by processes for mixing, stirring or dispersing compressed gases, such as air, chlorofluorocarbon-based compounds, nitrogen, carbon dioxide, oxygen or helium, a process for mixing and stirring in the presence of a foaming agent, such as a surfactant.

In particular, the composition in the foam form is prepared by mixing the ingredients with stirring, generally under hot conditions, and by then expanding in volume under the action of a gas, it being possible for the gas to be introduced during the stage of cooling the composition or after preparation of the composition, for example using a device for expanding in volume of Mondomix type, a beater of Kenwood type, a scraped-surface exchanger or a dynamic mixer (of IMT type, for example). The gas is preferably air or nitrogen.

The composition according to the invention can be packaged in a container delimiting at least one compartment which comprises the composition, the container being closed by a closure part. The container can be equipped with a means for the dispensing of the product.

The container can be a pot.

The container can be at least partly made of thermoplastic. Mention may be made, as examples of thermoplastics, of polypropylene or polyethylene. Alternatively, the container is made of nonthermoplastic material, in particular of glass or metal (or alloy).

The composition can be applied, e.g., by finger or using an applicator.

The container is preferably used in combination with an applicator comprising at least one application component configured in order to apply the composition to keratinous substances.

According to another advantageous embodiment, the applicator comprises an application nozzle.

The foam composition according to the invention comprises from 1 to 30%, preferably from 3 to 10% by weight relative to the weight of the composition of microcapsules. The obtained foam is fine (small bubbles) and contains colored microcapsules. The said foam has a white aspect before application on keratinic materials and a colored aspect after application and homogenization on the keratinic materials, in particular skin.

When the foam composition comprises at least 3% by weight relative to the weight of the composition of microcapsules, it preferably comprises fillers and/or pigments, such as $TiO_2$, ZnO, CeO, Bismuth Oxichloride, Boron Nitrite, advantageously $TiO_2$.

The foam composition may also comprise calcium carbonate ($CaCO_3$) in order to avoid coloration of the water phase.

The foam composition according to the invention comprises from 1 to 10%, preferably from 3 to 8% by weight relative to the weight of the composition of fillers and/or pigments advantageously $TiO_2$.

The foam composition according to the invention comprises from 0.5 to 5%, preferably from 1 to 3% by weight relative to the weight of the composition of calcium carbonate.

In order to test the stability of the foams, they have been vigorously shaken (1000 shakes) the ΔE a,b between the color of the bulk before shaking and after shaking is less than 10, preferably less than 5.

According to another embodiment, the changing color composition according to the invention is an oil in water (O/W) emulsion.

This make up composition, which is preferably a makeup BB product for face or a foundation, provides very strong moisturizing sensation, creamy texture with very comfortable feeling during application, and sheer natural makeup result after application. After application, all these features help to deliver a very good balance of skincare efficacy perception (creamy and moisturization) as well as makeup efficacy (proper coverage and natural radiance). Advantageously, an appropriate sunscreen agent may be added.

This composition mainly comprises water, at least one non-volatile oil at least one O/W emulsifier and microcapsules.

The non-volatile oil(s) used in this preferred embodiment are the ones previously cited.

Advantageously the O/W emulsion contains a swelling agent, this agent allow a better swelling of the microcapsules thus rendering the microcapsules easier to break during application. Water, alcohols, glycols, polyols may be used as swelling agent.

Preferably the O/W emulsion also contains a co-emulsifier and/or a solubilizer.

Cetyl alcohol and stearyl alcohol may be cited as co-emulsifiers.

The solubilizer may be added in order to keep the properties of the O/W emulsion on storage, in particular to solubilize the ingredients of the water phase, to make and keep the composition stable in shelf lives. Polysorbate 20, PEG-60 hydrogenated castor oil may be mentioned as examples of solubilizers.

An O/W emulsion with perfect stable capsules in storage, with pigments releasing during application without any particle feeling is obtained. Makeup results are perfectly and evenly provided after application.

Moreover O/W emulsion may contain at least one of the following swelling agent, water such as deionized water, preferably in a concentration from 0 to 90% wgt, more preferably from 30 to 70% wgt, alcohols preferably in a concentration from 0 to 50% wgt, more preferably from 1 to 20% wgt, glycols such as propylene glycol, butylenes glycol, preferably in a concentration from 0 to 50% wgt, more preferably from 1 to 15% wgt, polyols such as glycerin, tetraols, preferably in a concentration from 0 to 50% wgt, more preferably from 1 to 10% wgt, co-emulsifier such as cetyl alcohol and stearyl alcohol, at high temperature above 60° C., preferably in a concentration from 0 to 20% wgt, more preferably from 1 to 5% wgt and solubilizer such as PEG-60 hydrogenated castor oil in a concentration from 0 to 10% wgt, more preferably from 1 to 5% wgt.

Otherwise, the O/W emulsion may contain at least two different types of microcapsules for example three different types of microcapsules. Thus the makeup results may be modified into natural and radiant look, further delivering a kind of look of white pinkish makeup with even skin tone.

Microcapsules such as Magic 60-WP0105, and Magic50-BW0105 from Korea Particle Technology from KPT, preferably in a concentration from 0 to 30% wgt, more preferably from 0 to 10% wgt could be introduced at last step with gentle stirring but without side scrapper after emulsion is made.

O/W emulsion can be obtained with pure and clean appearance of bulk, with perfect stability under −20/20° C. (5 cycle), room temperature (25° C., 2 months), 37° C. (2 months) and 45° C. (2 months). However, capsules would release pigments during application without any particle feeling. Makeup results are perfectly and evenly provided after application.

Moreover, organic sun filter can be added in the system and provide additional sun care benefit.

Advantageously the O/W emulsion contains at least non-entrapped $TiO_2$. The non-entrapped $TiO_2$ allowing a better covering effect.

Particularly the composition on the form of an emulsion comprises at least non-entrapped TiO2 and from 1 to 30% by weight relative to the weight of the composition of microcapsules.

Throughout the description, including the claims, the term "comprising a" should be understood as being synonymous with "comprising at least one", unless otherwise mentioned.

The terms "between . . . and . . . " and "ranging from . . . to . . . " should be understood as being inclusive of the limits, unless otherwise specified.

The invention is illustrated in greater detail by the examples according to the invention described below. Unless otherwise mentioned, the amounts indicated are expressed as mass percentages of active material.

EXAMPLES

I Microcapsules

Different examples of preparation of microcapsules according to the invention are here below described for illustrating the invention.

Example 1: Preparation of a Microcapsule Having Inner Brown Color Coating and Outer White Color Coating Mannitol (spray dried mannitol: Pearitol 100SD) is used as core.

To a mixed solution of 1600.0 g of methylene chloride and 1600.0 g of ethanol, 120.0 g of ceramide (Ceramide PC 104) and 120.0 g of hydrogenated lecithin (Lipoid S 100-3) are added and completely dissolved at 40° C. To the resulting mixture, 1260.0 g of iron oxide yellow, 252.0 g of iron oxide red and 45.36 g of iron oxide black are added and well dispersed with a homogenizer to prepare an inner color coating solution.

347.70 g of Mannitol is introduced into a fluidized bed coating system (Glatt GPOG 1, bottom spray) as a seed and subjected to a coating at 500 Ml/h of feeding rate of the inner color coating solution to obtain particles having a mannitol core coated with an inner color layer.

Thereafter, to a mixed solution of 720.0 g of methylene chloride and 720.0 g of ethanol, 36.0 g of ceramide and 36.0 g of hydrogenated lecithin are added and dissolved at 40° C. To the resulting mixture, 600.0 g of titanium dioxide particles are added and well dispersed with a homogenizer to prepare a titanium dioxide particle coating solution.

A coating with the resulting titanium dioxide particle coating solution is realized by a fluidized bed process to obtain particles having an inner color layer coated with a titanium dioxide particle layer.

Then, 300.0 g of shellac is dissolved in 3000 g of ethanol to prepare an outer layer coating solution, which is coated onto the above titanium dioxide particle layer to obtain a color-changing microcapsule having a titanium dioxide particle layer coated with an outer layer.

Example 2: Preparation of a Microcapsule Having Inner Yellow Color Coating and Outer White Color Coating A microcapsule is prepared in the same manner as in Example 1 except for using 1557.36 g of iron oxide yellow instead of the mixed colorants consisting of iron oxide yellow, iron oxide red and iron oxide black as the inner color in the preparation of the inner color coating solution.

Example 3: Preparation of a Microcapsule Having Inner Red Color Coating and Outer White Color Coating A microcapsule is prepared in the same manner as in Example 1 except for using 1557.36 g of iron oxide red instead of the mixed colorants consisting of iron oxide yellow, iron oxide red and iron oxide black as the inner color in the preparation of the inner color coating solution.

Example 4: Preparation of a Microcapsule Having Inner Black Color Coating and Outer White Color Coating A microcapsule is prepared in the same manner as in Example 1 except for using 1557.36 g of iron oxide black instead of the mixed colorants consisting of iron oxide yellow, iron oxide red and iron oxide black as the inner color in the preparation of the inner color coating solution.

Example 5: Preparation of a Microcapsule Having Inner Black Color Coating and Outer Green Color Coating The same procedure as in Example 4 is repeated to the step for forming a titanium dioxide particles layer.

Thereafter, to a mixed solution of 400.0 g of methylene chloride and 400.0 g of ethanol, 20.0 g of ceramide and 20.0 g of hydrogenated lecithin are added and dissolved at 40° C. To the resulting reaction mixture, 40.0 g of chromium hydroxide green (CI77289) is added and well dispersed with a homogenizer to prepare a green color coating solution.

A coating with the resulting green color coating solution is realized by a fluidized bed process at 500 Ml/h of feeding rate of the coating solution to obtain particles having a titanium dioxide particle layer coated with a green color layer.

Then, 200.0 g of polymethacrylate (Eudragit RSPO) is dissolved in 4000 g of ethanol to prepare an outer layer coating solution. A coating with the resulting outer layer coating solution is realized by a fluidized bed process at 100 Ml/h of feeding rate of the coating solution to obtain a color-changing microcapsule having a green color layer coated with a polymeric outer layer.

Example 6

Figure 2:
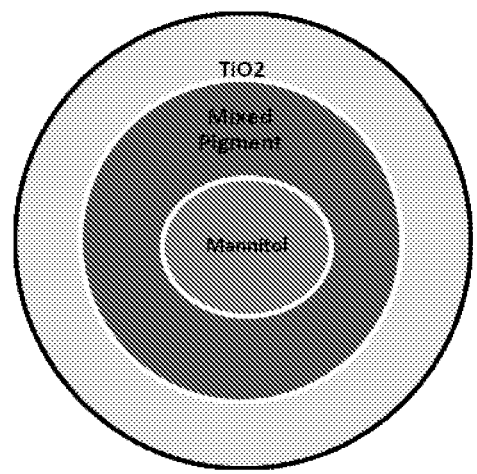
FIGS. 2 to 10 represent a schematic diagram showing the core-shell structure of color-changing microcapsules prepared according to Examples 6 to 14, respectively, which are described later in this description.

By using the ingredients and contents described in the below table, a color-changing microcapsule having a core and 2 layers as shown in FIG. 2 is prepared by a fluidized bed process:

(1) Mixed Pigment (Inner color): Yellow:Red:Black=55.18:34.48:10.34

(2) Ingredients: Core seed—Inner color layer—$TiO_2$ particle layer

| Core | Mannitol | 16.45% |
|---|---|---|
| $1^{st}$ layer | Mixed Pigment | 50.0% |
| | Lecithin | 0.4% |
| | Corn Starch binder | 2.0% |
| $2^{nd}$ layer | Titanium dioxide | qsp. 100% |
| | Lecithin | 0.2% |
| | Corn Starch binder | 0.8% |

Percentages indicate weight percent relative to the total microcapsule weight.

Example 7

Figure 3:
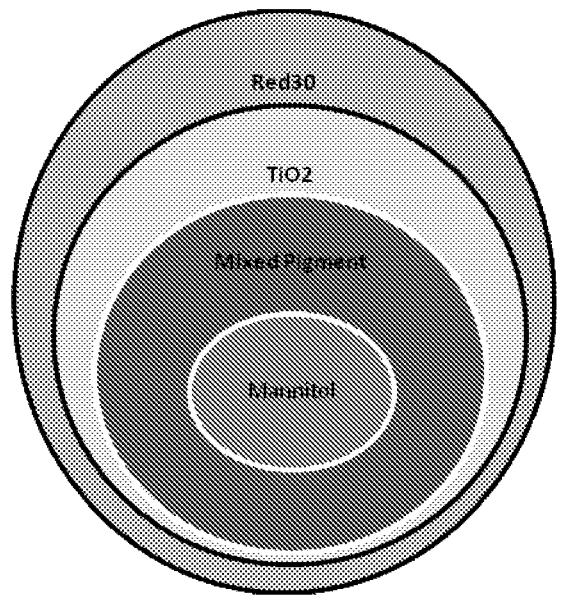

By using the ingredients and contents described in the below table, a color-changing microcapsule having a core and 3 layers as shown in FIG. 3 is prepared by a fluidized bed process:

(1) Mixed Pigment (Inner color): Yellow:Red:Black=60.4:23.8:11.4:4.4

(2) Ingredients: Core seed—Inner color layer—TiO₂ particle layer—outer color layer

| Core | Mannitol | 6.5% |
|---|---|---|
| 1st layer | Mixed Pigment | 17.8% |
| | Sunpuro Yellow | 2.00% |
| | Lecithin | 5.0% |
| | Eudragit RSPO | 4.0% |
| 2nd layer | Titanium dioxide | qsp. 100% |
| | Lecithin | 5.0% |
| | Eudragit RSPO | 4.0% |
| 3rd layer | D&C Red30 | 0.8% |
| | Cornstarch binder | 0.4% |

Percentages indicate weight percent relative to the total microcapsule weight.

Example 8

Figure 4:
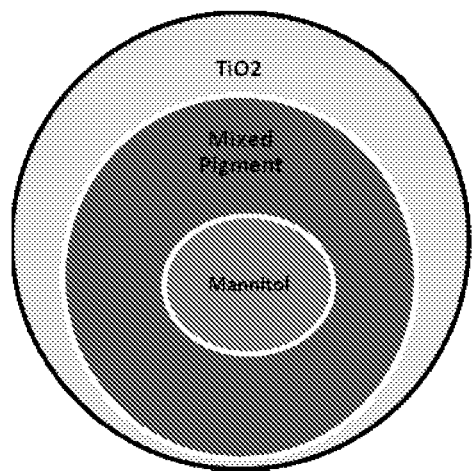

By using the ingredients and contents described in the below table, a color-changing microcapsule having a core and 2 layers as shown in FIG. 4 is prepared by a fluidized bed process:

(1) Mixed Pigment (Inner color): Yellow:Red:Black=60.1:28.8:11.1

(2) Ingredients: Core seed—inner color layer—TiO₂ particle layer

| Core | Mannitol | 17.8% |
|---|---|---|
| 1st layer | Mixed Pigment | 19.8% |
| | Lecithin | 0.2% |
| | Corn Starch binder | 0.8% |
| 2nd layer | Titanium dioxide | qsp. 100% |
| | Mannitol | 5.0% |
| | Corn Starch | 5.0% |
| | Lecithin | 0.3% |
| | Corn Starch binder | 1.2% |

Percentages indicate weight percent relative to the total microcapsule weight.

Example 9

Figure 5:
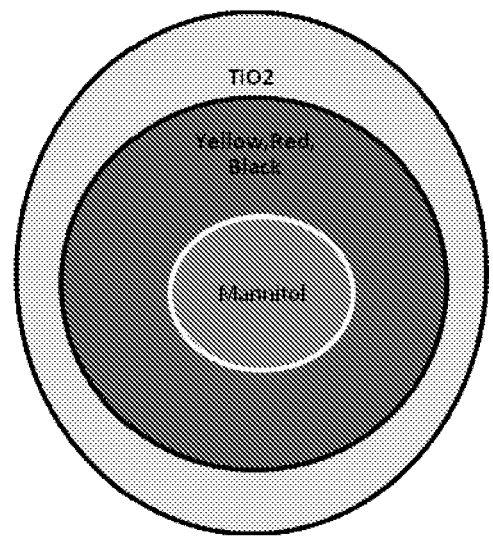

By using the ingredients and contents described in the below table, a color-changing microcapsule having a core and 2 layers as shown in FIG. 5 is prepared by a fluidized bed process:

(1) Ingredients: Core seed—inner color layer—TiO₂ particle layer

| Core | Mannitol | 13.7% |
|---|---|---|
| 1st layer | Sunpuro Yellow | 17.36% |
| | Sunpuro Red | 3.67% |
| | Sunpuro Black | 0.61% |
| | Lecithin | 0.20% |
| | Corn Starch Binder | 1.0% |
| 2nd layer | Titanium dioxide | qsp.100% |
| | Lecithin | 0.3% |
| | Corn Starch Binder | 1.5% |

Percentages indicate weight percent relative to the total microcapsule weight.

Example 10

Figure 6:
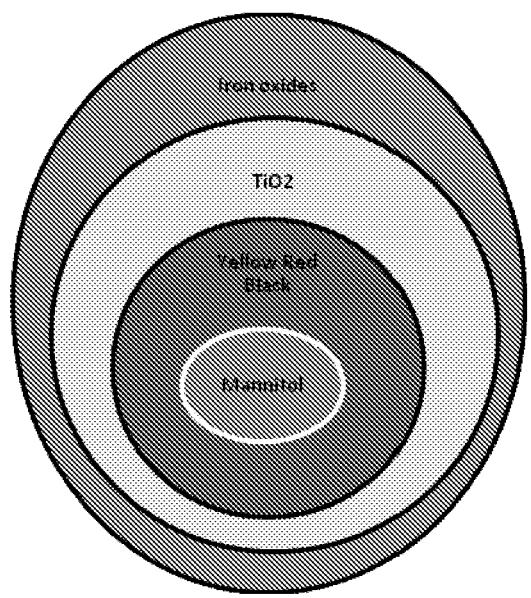

By using the ingredients and contents described in the below table, a color-changing microcapsule having a core and 3 layers as shown in FIG. 6 is prepared by a fluidized bed process:

(1) Mixed Pigment (Inner color): Yellow:Red:Black=55.18:34.48:10.34

(2) Ingredients: Core seed—Inner color layer—TiO₂ particle layer—Outer color layer

| Core | Mannitol | 16.81% |
|---|---|---|
| 1st layer | Mixed Pigment | 49.15% |
| | Lecithin | 0.29% |
| | Corn Starch Binder | 1.97% |
| 2nd layer | Titanium dioxide | qsp 100% |
| | Lecithin | 0.1% |
| | Corn Starch Binder | 0.49% |
| 3rd layer | Sunpuro Yellow | 1.0% |
| | Sunpuro Red | 0.2% |
| | Corn Starch Binder | 0.5% |

Percentages indicate weight percent relative to the total microcapsule weight.

Example 11

Figure 7:
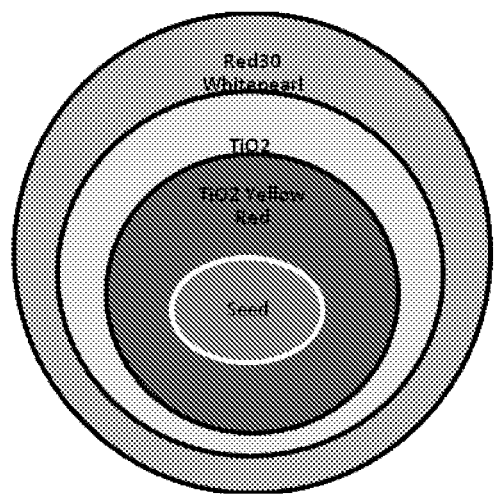

By using the ingredients and contents described in the below table, a color-changing microcapsule having a core and 3 layers as shown in FIG. 7 is prepared by a fluidized bed process:

(1) Mixed Pigment (Inner color): White:Yellow:Red=92:6:2

(2) Ingredients: Core seed—Inner color layer—TiO₂ particle layer—Outer color layer

| | | | | |
|---|---|---|---|---|
| Core | | 4.0% | Cellulose | 1.12% |
| | | | Mannitol | 1.0% |
| | | | Zea Mays (corn) starch | 1.84% |
| | | | Hydrogenated Lecithin | 0.04% |
| 1st layer | Mixed Pigment | 55.0% | Titanium Dioxide | 50.6% |
| | | | Iron oxide Yellow | 3.3% |
| | | | Iron oxide Red | 1.1% |
| | Lecithin | 0.50% | Hydrogenated Lecithin | 0.50% |
| | Mannitol | 3.5% | Mannitol | 3.5% |
| | Corn Starch Binder | 2.0% | Zea Mays (corn) starch | 2.0% |
| 2nd layer | Titanium dioxide | qsp 100%. | Titanium dioxide | qsp 100%. |
| | Corn Starch | 3.62% | Zea Mays (corn) starch | 3.62% |
| | Cellulose | 9.0% | Cellulose | 9.0% |
| | Mannitol | 13.0% | Mannitol | 13.0% |
| | Lecithin | 0.25% | Hydrogenated Lecithin | 0.25% |
| | Corn Starch Binder | 1.8% | Zea Mays (corn) starch | 1.8% |
| 3rd Layer | Satin White | 1.8% | Synthetic Fluorphlogopite | 1.035% |
| | | | Tin oxide | 0.009% |
| | | | Titanium Dioxide | 0.756% |
| | D&C Red30 | 0.03% | Red30 Al. Lake | 0.03% |
| | Corn Starch Binder | 0.5% | Zea Mays (corn) starch | 0.5% |

Percentages indicate weight percent relative to the total microcapsule weight.

Example 12

Figure 8:
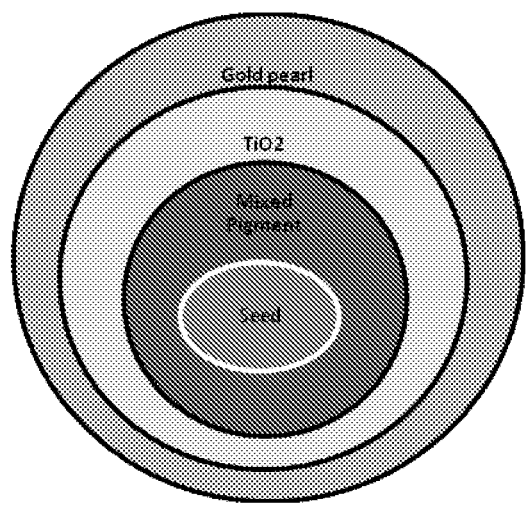

By using the ingredients and contents described in the below table, a color-changing microcapsule having a core and 3 layers as shown in FIG. 8 is prepared by a fluidized bed process:

(1) Mixed Pigment (Inner color): White:Yellow:Red:Black=89:2:8:1

(2) Ingredients: Core seed—Inner color layer—TiO₂ particle layer—Outer color layer

| Core | | 34.4% |
|---|---|---|
| 1st layer | Mixed Pigment | 50.0% |
| | Lecithin | 0.50% |

-continued

| | | | | |
|---|---|---|---|---|
| | | Mannitol | 4.0% | |
| | | Corn Starch Binder | 2.0% | |
| 2nd layer | | Titanium dioxide | qsp 100% | |
| | | Lecithin | 0.1% | |
| | | Corn Starch Binder | 0.4% | |
| 3rd Layer | | C. Monarch gold | 3.0% | |
| | | Corn Starch Binder | 0.6% | |

Percentages indicate weight percent relative to the total microcapsule weight.

(3) Ingredient of each layer (in details):

| Core | | 34.4% | Zea Mays (corn) Starch | 14.3% |
|---|---|---|---|---|
| | | | Mannitol | 10.5% |
| | | | Cellulose | 9.6% |
| 1st layer | Mixed Pigment | 50.0% | Titanium Dioxide | 44.5% |
| | | | Iron oxide Yellow | 4.0% |
| | | | Iron oxide Red | 1.0% |
| | | | Iron oxide Black | 0.5% |
| | Lecithin | 0.50% | Hydrogenated Lecithin | 0.50% |
| | Mannitol | 4.0% | Mannitol | 4.0% |
| | Corn Starch Binder | 2.0% | Zea Mays (corn) Starch | 2.0% |
| 2nd layer | Titanium dioxide | qsp. 100% | Titanium dioxide | qsp. 100% |
| | Lecithin | 0.1% | Hydrogenated Lecithin | 0.1% |
| | Corn Starch Binder | 0.4% | Zea Mays (corn) Starch | 0.4% |
| 3rd Layer | C.Monarch gold | 3.0% | Mica | 1.575% |
| | | | Titanium Dioxide | 1.29% |
| | | | Iron oxide Red | 0.12% |
| | | | Tin Oxide | 0.015% |
| | Corn Starch Binder | 0.6% | Zea Mays (corn) Starch | 0.6% |

Percentages indicate weight percent relative to the total microcapsule weight.

Example 13

Figure 9:
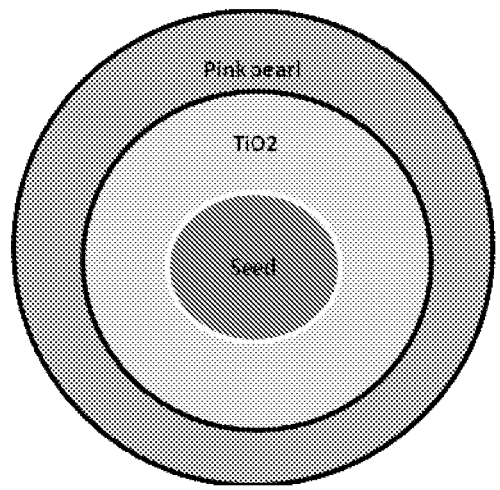

By using the ingredients and contents described in the below table, a color-changing microcapsule having a core and 2 layers as shown in FIG. 9 is prepared by a fluidized bed process:

(1) Ingredients: Core seed—White $TiO_2$ particle layer—Outer color layer

| Core | Mannitol | 27.85% |
|---|---|---|
| 1st layer | Titanium dioxide | qsp. 100% |
| | Lecithin | 0.5% |
| | Corn Starch Binder | 1.5% |
| 2nd layer | D&C Red30 | 0.145% |
| | Satin White | 4.55% |
| | Corn Starch Binder | 0.3% |

Percentages indicate weight percent relative to the total microcapsule weight.

(2) Ingredient of each layer (in details):

| Core | Mannitol | 27.85% | Mannitol | 27.85% |
|---|---|---|---|---|
| 1st layer | Titanium dioxide | qsp. | Titanium dioxide | qsp. 100% |
| | Lecithin | 0.5% | Lecithin | 0.5% |
| | Corn Starch Binder | 1.5% | Corn Starch Binder | 1.5% |
| 2nd layer | D&C Red30 | 0.145% | D&C Red30 | 0.145% |
| | Satin White | 4.55% | Synthetic Fluorphlogopite | 2.66% |
| | | | Tin oxide | 0.023% |
| | | | Titanium Dioxide | 1.867% |
| | Corn Starch Binder | 0.3% | Corn Starch Binder | 0.3% |

Percentages indicate weight percent relative to the total microcapsule weight.

Example 14

Figure 10:
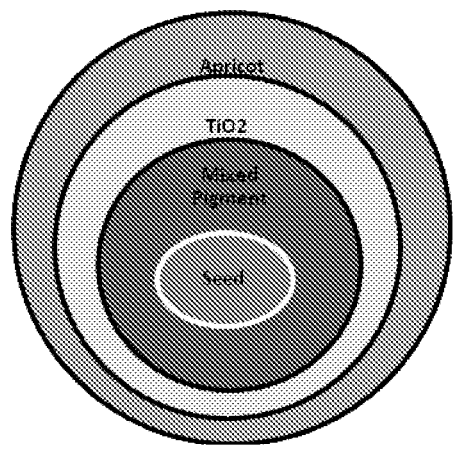

By using the ingredients and contents described in the below table, a color-changing microcapsule having a core and 3 layers as shown in FIG. 10 is prepared by a fluidized bed process:

(1) Mixed Pigment: White:Yellow:Red:Black=84.3:5.0:8.7:2

(2) Ingredients: Core seed—Inner color layer—$TiO_2$ particle layer—Outmost shell

| Core | | 4.0% | Cellulose | 1.0% |
|---|---|---|---|---|
| | | | Mannitol | 1.0% |
| | | | Zea Mays (corn) Starch | 2.0% |
| 1st layer | Mixed Pigment | 50.0% | Titanium dioxide | 42.15% |
| | | | Iron oxide Yellow | 2.5% |
| | | | Iron oxide Red | 4.35% |
| | | | Iron oxide Black | 1.0% |
| | Lecithin | 0.50% | Hydrogenated Lecithin | 0.50% |
| | Mannitol | 3.5% | Mannitol | 3.5% |
| | Corn Starch Binder | 2.0% | Zea Mays (corn) Starch | 2.0% |
| 2nd layer | Titanium dioxide | qsp. 100% | Titanium dioxide | qsp. 100% |
| | Corn Starch | 2.0% | Zea Mays (corn) Starch | 2.0% |
| | Cellulose | 5.0% | Cellulose | 5.0% |
| | Mannitol | 6.5% | Mannitol | 6.5% |
| | Lecithin | 0.25% | Hydrogenated Lecithin | 0.25% |
| | Corn Starch Binder | 1.0% | Zea Mays (corn) Starch | 1.0% |
| 3rd Layer | Iron oxide Red | 0.05% | Iron oxide Red | 0.05% |
| | Iron oxide Yellow | 0.01% | Iron oxide Yellow | 0.01% |
| | Cellulose | 5.0% | Cellulose | 5.0% |
| | Mannitol | 6.5% | Mannitol | 6.5% |
| | Corn Starch | 7.44% | Zea Mays (corn) Starch | 7.44% |
| | Lecithin | 0.25% | Hydrogenated Lecithin | 0.25% |
| | Corn Starch Binder | 1.0% | Zea Mays (corn) Starch | 1.0% |

Percentages indicate weight percent relative to the total microcapsule weight.

II Compositions

In all examples, «alcohol» means «ethanol».

When not specified, the protocol used to prepare the compositions is a conventional protocol.

Example 1: Foundation

| Chemical names | % weight |
|---|---|
| Magnesium Sulfate, 7 H2O | 0.70 |
| Modified Hectorite distearyl dimethyl ammonium | 0.80 |
| Talc: micronized magnesium silicate (particle size: 5 microns) (ci: 77718) | 0.50 |
| Pink microcapsule containing titanium dioxide, mannitol, hydrogenated lecithin, synthetic fluorphlogopite, red 30 lake, zea mays (corn) starch, tin oxide (Magic 60-WP0105 ® from KPT) | 2.00 |
| Ash gray microcapsule containing mannitol, iron oxide red, iron oxide yellow, iron oxide black, hydrogenated lecithin, titanium dioxide, zea mays (corn) starch (Magic 50-BW0105 ® from KPT) | 2.00 |
| Refined plant Perhydrosqualene | 1.00 |
| Protected 2-ethyl hexyle 4-methoxycinnamate | 3.00 |
| Bismuth oxychloride and ethylhexyl hydroxystearate (Timiron liquid silver ® from merck) | 3.00 |
| Microspheres of nylon-12 (particle size: 5 microns) | 0.50 |
| Phenyl trimethylsiloxy trisiloxane (viscosity: 20 cst-pm: 372) | 2.00 |

-continued

| Chemical names | % weight |
|---|---|
| Poly dimethylsiloxane with alpha-omega oxyethylene/ oxypropylene groups in solution in cyclopentasiloxane | 1.00 |
| Poly dimethylsiloxane oxyethylene (dp: 70-viscosity: 500 cst) | 2.00 |
| Polydimethylsiloxane 2 cst | 27.98 |
| 1,3-butylene glycol | 3.00 |
| Denatured Ethyl Alcohol 96 degrees | 5.00 |
| Hydrophilic gelifying agent | 1.00 |
| Water | qsp 100 |

Protocol of Preparation

Aqueous phase (water, butylene glycol, magnesium sulfate) and fatty phase (silicone surfactants, oils, fillers) are prepared separately.

Both phases are then mixed under Moritz agitation until homogenization.

Then the bismuth oxychloride dispersed in ethylhexylhydroxystearate is added under Moritz agitation until homogenization.

Then the alcohol is added under Moritz agitation.

The microcapsules are then added under low Rayneri agitation until homogenization.

Observations

The composition in the jar or on finger has a white pearly aspect, the microcapsules being covered by the bismuth oxychloride pre-dispersion.

After application and homogenization on the skin, the said composition gives a unifying and luminous make-up effect.

Example 2: Transparent Gel with Brown Microcapsules for Make-Up Result

| Phase | INCI name | % weight |
|---|---|---|
| A1 | WATER | qsp 100 |
| | ACRYLATES/C10-30 ALKYL ACRYLATE CROSSPOLYMER (CARBOPOL ULTREZ 20 POLYMER ® from LUBRIZOL) | 0.70 |
| A2 | GLYCERIN | 4.00 |
| | DISODIUM EDTA | 0.15 |
| | BUTYLENE GLYCOL | 6.00 |
| | CAPRYLYL GLYCOL | 0.25 |
| B | WATER | 31.00 |
| | BIS-PEG-18 METHYL ETHER DIMETHYL SILANE (DOW CORNING 2501 COSMETIC WAX ® from Dow Corning) | 2.00 |
| C | WATER | 3.00 |
| D1 | BIOSACCHARIDE GUM-1 | 1.00 |
| | PEG/PPG/POLYBUTYLENE GLYCOL-8/5/3 GLYCERIN (WILBRIDE S-753L ® from Nof Corporation) | 0.70 |
| D2 | ALCOHOL | 4.00 |
| E | TITANIUM DIOXIDE (and) IRON OXIDES (and) MANNITOL (and) IRON OXIDES (and) ZEA MAYS (CORN) STARCH (and) IRON OXIDES (and) HYDROGENATED LECITHIN (Magic50-BW0105 ® from KPT) | 2 |

Protocol of Preparation:

Premix B at 70° C., mix until solution is clear

Main Mix

1. Phase A1 make the polymer well swelled in water, then, heat to 80° C.-85° C.

2. Add A2, mix until fully dissolved

3. Add phase B, fully dissolved, then cool to RT

4. Below 40° C., add in phase C.

5. Vacuum and slow mix, to reduce the gas bubbles in the bulk

6. Add phase D1, D2

7. Vacuum and slow mix, until temp to RT, and with few gas bubbles

8. Slowly add phase E (microcapsules), mix without scraper.

9. When microcapsules are fully dispersed evenly, stop mixing, check the pH and viscosity The viscosity of the gel is around 20 UD (Mobile 3) by Rheomat RM180, at 25° C. according to the protocol disclosed above.

Aspect of the Composition and Evaluation after Application

The gel presents a transparent and caring appearance and also covering makeup effects.

We obtain a gel with colored microcapsules in pure and clean appearance, with perfect stability under −20/20° C. (5 cycle), room temperature (25° C., 2 months), 37° C. (2 months) and 45° C. (2 months). The microcapsules release pigments during application on the skin with comfortable feeling during application, and confer natural make-up result as it was a foundation, but with a very good balance of skincare efficacy perception (watery, moisturization and transparent) as well as makeup efficacy (proper coverage).

Example 3: O/W Emulsion with Pink Microcapsules

| Phase | INCI name | % weight |
|---|---|---|
| A1 | GLYCERIN | 8.00 |
| | WATER | qsp 100 |
| | PRESERVATIVES | 0.50 |
| | PROPYLENE GLYCOL | 8.00 |
| A2 | POTASSIUM CETYL PHOSPHATE | 1.00 |
| B1 | STEARIC ACID | 2.00 |
| | GLYCERYL STEARATE (and) PEG-100 STEARATE | 1.50 |
| | CETYL ALCOHOL | 0.70 |
| | OCTYLDODECANOL | 4.00 |
| | ETHYLHEXYL METHOXYCINNAMATE | 9.50 |
| B2 | TRIETHANOLAMINE | 0.40 |
| | PHENOXYETHANOL | 0.70 |
| B3 | CYCLOHEXASILOXANE | 4.00 |
| B4 | TITANIUM DIOXIDE (and) C9-15 FLUOROALCOHOL PHOSPHATE (and) ALUMINUM HYDROXIDE | 2.00 |
| C | CYCLOHEXASILOXANE | 3.00 |
| | CARBOMER | 0.30 |
| | XANTHAN GUM | 0.10 |
| D | WATER | 1.00 |
| | TRIETHANOLAMINE | 0.30 |
| E | TALC | 0.50 |
| F | TITANIUM DIOXIDE (and) MANNITOL (and) HYDROGENATED LECITHIN (and) IRON OXIDES (and) SYNTHETIC FLUORPHLOGOPITE (and) IRON OXIDES (and) RED 30 LAKE (and) IRON OXIDES (and) TIN OXIDE (and) ZEA MAYS (CORN) STARCH (Magic 60-WP0105 ® from KPT) | 1.00 |
| | BISMUTH OXYCHLORIDE | 5.00 |

Protocol of Preparation:

1. mixing phase A1 to 75° C.

2. add A2 into A1

3. B3+B4 roll miller

4. Mixing B1+B2+B3+B4 to 75° C.

5. Add Phase B into phase A, homogenize (Rayneri 1000 rpm, 10 min)

6. Cool down to 65° C. add phase C, phase D (1800 rpm, 15 min)

7. Cool down to 45° C. add Phase E

8. Change Rayneri to Ekart, using a small blender, add phase F until the microcapsules are even dispersed.

Aspect of the Composition and Evaluation after Application

The O/W emulsion obtained presents a white-pinkish and caring appearance but with covering makeup effect when applied on the skin.

The O/W emulsion has a pure and clean appearance in the jar, with perfect stability under −20/20° C. (5 cycle), room temperature (25° C., 2 months), 37° C. (2 months) and 45° C. (2 months). The microcapsules release pigments during application on the skin with comfortable feeling during application, and confer natural make-up result as it was a foundation, but with a very good balance of skincare efficacy perception (watery, moisturization and transparent) as well as makeup efficacy (proper coverage).

Example 4: Skin Care Gel

| INCI name | % weight |
|---|---|
| WATER | Qsp 100 |
| GLYCERIN | 4 |
| DISODIUM EDTA | 0.15 |
| NIACINAMIDE | 4 |
| BUTYLENE GLYCOL | 7 |
| CHLORPHENESIN | 0.25 |
| ACRYLATES/C10-30 ALKYL ACRYLATE CROSSPOLYMER (CARBOPOL ULTREZ 20 POLYMER ® from LUBRIZOL) | 0.7 |
| BIS-PEG-18 METHYL ETHER DIMETHYL SILANE | 2 |
| PEG-60 HYDROGENATED CASTOR OIL | 0.1 |
| BIOSACCHARIDE GUM-1 | 1 |
| SODIUM HYDROXIDE | 0.24 |
| ALCOHOL | 5 |
| CAPRYLOYL SALICYLIC ACID | 0.15 |
| TITANIUM DIOXIDE (and) MANNITOL (and) HYDROGENATED LECITHIN (and) IRON OXIDES (and) SYNTHETIC FLUORPHLOGOPITE (and) IRON OXIDES (and) RED 30 LAKE (and) IRON OXIDES (and) TIN OXIDE (and) ZEA MAYS (CORN) STARCH (Magic 60-WP0105 ® from KPT) | 0.5 |
| TITANIUM DIOXIDE (and) IRON OXIDES (and) MANNITOL (and) IRON OXIDES (and) ZEA MAYS (CORN) STARCH (and) IRON OXIDES (and) HYDROGENATED LECITHIN (Magic50-BW0105 ® from KPT) | 0.2 |

The gel is prepared as the one disclosed in example 2.

After application on the skin, natural make-up result is obtained with a good balance of skincare efficacy perception (watery, moisturization and transparent) as well as makeup efficacy (proper coverage).

Example 5: Gelly Skin Care Cream

| INCI NAME | % weight |
|---|---|
| WATER | Qsp 100 |
| GLYCEROL | 4 |
| 1,3-BUTYLENE GLYCOL | 8 |
| VITAMINE B3 OR PP: NICOTINIC ACID AMIDE | 4 |
| ETHYLENE DIAMINE TETRACETIC ACID, DISODIUM SALT, 2 H2O | 0.1 |
| CARBOXYVINYLIC POLYMER SYNTHETIZED IN METHYLENE CHLORIDE | 0.6 |
| POLY DIMETHYLSILOXANE (VISCOSITY: 10 CST) | 1 |
| MIXTURE OF RETICULATED POLY DIMETHYLSILOXANE POLYALKYLENE AND POLY DIMETHYLSILOXANE (6 CST) 27/73 | 0.8 |
| MIXTURE OF POLY DIHYDROXYLATED DIMETHYLSILOXANE ALPHA-OMEGA/POLY DIMETHYLSILOXANE 5 CST | 1.2 |
| n-OCTANOYL-5 SALICYLIC ACID | 0.15 |
| NO DENATURATED ABSOLUTE ETHYL ALCOHOL | 5 |
| TITANIUM DIOXIDE (and) IRON OXIDES (and) MANNITOL (and) IRON OXIDES (and) ZEA MAYS (CORN) STARCH (and) IRON OXIDES (and) HYDROGENATED LECITHIN (Magic50-BW0105 ® from KPT) | 0.5 |

This composition is obtained according to classical method. After application on the skin, an healthy effect is obtained with a good balance of skincare efficacy perception (watery, moisturization and transparent) as well as makeup natural effect.

Example 6: Emulsion (O/W) for Eyes

| INCI name | % weight |
|---|---|
| DISODIUM EDTA | 0.1 |
| TITANIUM DIOXIDE (and) MANNITOL (and) HYDROGENATED LECITHIN (and) IRON OXIDES (and) SYNTHETIC FLUORPHLOGOPITE (and) IRON OXIDES (and) RED 30 LAKE (and) IRON OXIDES (and) TIN OXIDE (and) ZEA MAYS (CORN) STARCH (Magic 60-WP0105 ® from KPT) | 0.18 |
| PHENOXYETHANOL | 0.8 |
| CAPRYLIC/CAPRIC TRIGLYCERIDE | 1.26 |
| TITANIUM DIOXIDE (and) MICA (and) SILICA (TIMIRON SPLENDID COPPER ® FROM Merck) | 0.7 |
| PTFE (POLYTETRAFLUOROETHYLENE) | 1.5 |
| AMMONIUM POLYACRYLOYLDIMETHYL TAURATE | 1 |
| PEG-12 DIMETHICONE | 0.6 |
| DIMETHICONE (and) DIMETHICONOL (XIAMETER PMX-1503 FLUID ® from Dow Corning) | 2.5 |
| POLYMETHYLSILSESQUIOXANE (Tospearl 200B ® from Momentive Performance Materials) | 1.5 |
| POLYSILICONE-11 (GRANSIL RPS-D6 ® from Grant Industries) | 21 |
| ETHANOL | 4 |
| WATER | Qsp 100 |
| GLYCERIN | 8 |

This O/W emulsion is obtained according to classical method.

The cream is applied around the eye and confers a natural skin and make-up effect that diminishes the visibility of dark circles.

Example 7 Aerosol Foams

| Nom INCI | A | B | C | D | E |
|---|---|---|---|---|---|
| TITANIUM DIOXIDE (and) SILICA (and) ALUMINUM | 5.6 | 5.6 | 5.6 | 3.8 | 5.6 |

-continued

| Nom INCI | A | B | C | D | E |
|---|---|---|---|---|---|
| HYDROXIDE (and) ALGINIC ACID | | | | | |
| TALC | 2.20 | 2.20 | 2.20 | 9.50 | 2.20 |
| SILICA (and) METHICONE | 3.00 | 3.00 | 3.00 | 0.00 | 3.00 |
| CALCIUM CARBONATE | 2.00 | 2.00 | 2.00 | 0.00 | 2.00 |
| ETHYLHEXYL METHOXY-CINNAMATE | 7.50 | 7.50 | 7.50 | 7.50 | 7.50 |
| WATER | qsp 95 | qsp 95 | qsp 95 | qsp 95 | qsp 95 |
| HYDROPHILIC GELIFYING AGENT | 1.00 | 1.00 | 1.00 | 1.00 | 1.00 |
| DIPOTASSIUM GLYCYRRHIZATE | 0.20 | 0.20 | 0.20 | 0.20 | 0.20 |
| SODIUM HYALURONATE | 0.01 | 0.01 | 0.01 | 0.01 | 0.01 |
| BETAINE | 1.00 | 1.00 | 1.00 | 1.00 | 1.00 |
| GLYCERIN | 2.00 | 2.00 | 2.00 | 2.00 | 2.00 |
| ETHYLHEXYL-GLYCERIN | 0.20 | 0.20 | 0.20 | 0.20 | 0.20 |
| CAPRYLYL GLYCOL | 0.50 | 0.50 | 0.50 | 0.50 | 0.50 |
| BUTYLENE GLYCOL | 2.00 | 2.00 | 2.00 | 2.00 | 2.00 |
| ALCOHOL | 2.85 | 2.85 | 2.85 | 2.85 | 2.85 |
| PEG-12 DIMETHICONE | 0.95 | 0.95 | 0.95 | 0.95 | 0.95 |
| PHENOXYETHANOL | 0.285 | 0.285 | 0.285 | 0.285 | 0.285 |
| TITANIUM DIOXIDE (and) IRON OXIDES (and) MANNITOL (and)IRON OXIDES (and) ZEA MAYS (CORN)STARCH (and) IRONOXIDES (and) HYDROGENATED LECITHIN (*) | 3.80 | 8.55 | 13.30 | 3.80 | 20.00 |
| LPG (LIQUIFIED PETROLEUM GAS) | 5.00 | 5.00 | 5.00 | 5.00 | 5.00 |

(*) Magic50-BW0105 ® from KPT a) Procedure of Preparation
1. Powder phase is mixed by powder mixer
2. Mixed powder phase is added in main kettle
3. Heated water phase (75-85° C.) is added in main kettle
4. Heated oil phase (75-85° C.) is added in main kettle
5. Homogenized in main kettle
6. After mixing, cooled by room temperature
7. Added surfactant and fragrance phase in main kettle
8. Homogenized in main kettle
9. Add the microcapsules and mix gently with paddle
10. Finish to make bulk
(Filling Process)
11. Pour bulk in the aerosol package
12. Add LPG (propane/butane mixture (Liquified Petroleum Gas or LPG) in aerosol package (5%, 0.31 MPa)

With A-D compositions, the foams obtained are white, with composition E, a foam is obtained, the particles are quite invisible in the bulk They all confer a natural skin and make-up effect when applied on the skin.

What is claimed is:

1. A changing color composition, comprising, in a physiologically acceptable medium:
   a) microcapsules comprising:
      a core comprising one monosaccharide-polyol selected from the group consisting of mannitol, erythritol, xylitol, sorbitol and mixtures thereof, and
      a layered coating comprising at least two layers surrounding the core, the layered coating comprising a polymer, a colorant, and optionally a lipid-based material,
   b) at least 3% by weight, relative to a weight of the composition, of an aqueous phase comprising water and at least one compound selected from the group consisting of a polyol, a glycol and a $C_2$-$C_8$ monoalcohol,
   c) a hydrophilic gelifying agent, and
   d) optionally 0.1 to 70% by weight relative to the weight of the composition, of one or more additional cosmetic ingredients selected from the group consisting of a volatile or nonvolatile silicon or hydrocarbon oil, a surfactant, a filler, a thickening agent, a film forming agent, a polymer, a preservative, a silicone elastomer, a self-tanning agent, an additional non-entrapped colorant, a cosmetic active, a pH regulator, and a perfume,
   wherein
   the core does not comprise a colorant material, and
   the microcapsules comprise at least two layers of different colors.

2. The changing color composition according to claim 1, wherein the core comprises mannitol.

3. The changing color composition according to claim 1, wherein the layered coating surrounding the core comprises a hydrophilic polymer selected from the group consisting of:
   an acrylic acid homopolymer or salt thereof;
   an acrylic acid copolymer or salt thereof;
   a methacrylic acid homopolymer or salt thereof;
   a methacrylic acid copolymer or salt thereof;
   an ester of an acrylic acid homopolymer or copolymer;
   an ester of a methacrylic acid homopolymer or copolymer;
   a copolymer of acrylic acid and of acrylamide, or a salt or ester thereof;
   a polyhydroxycarboxylic acid, or a salt or ester thereof;
   a polyacrylic acid/alkyl acrylate copolymer;
   AMPS (polyacrylamidomethylpropanesulfonic acid partially neutralized with aqueous ammonia);
   an AMPS/acrylamide copolymer;
   a polyoxyethylenated AMPS/alkyl methacrylate copolymer;
   chitin or chitosan;
   a cellulose polymer or derivative thereof;
   a starch polymer or derivative thereof, optionally modified;
   a vinyl polymer or derivative thereof;
   an alginate or a carrageenan;
   a glycoaminoglycan, hyaluronic acid or a derivative thereof; and
   a mucopolysaccharide.

4. The changing color composition according to claim 1, wherein the hydrophilic gelifying agent is at least one selected from the group consisting of an acrylate/$C_{10}$-$C_{30}$-alkylacrylate copolymer, a polyacrylic acid (carbomer), xanthan gum, a carboxyvinylic polymer synthesized in methylene chloride, and ammonium polyacryloyldimethyltaurate.

5. The changing color composition according to claim 1, wherein a weight % of the colorant is from 20% to 90% by weight relative to the weight of the microcapsule.

6. The changing color composition according to claim 1, wherein the multi-layered coating surrounding the core comprises three or more layers of different colors.

7. The changing color composition according to claim 1, wherein the microcapsules further comprise a lipid based material.

8. The changing color composition according to claim 1, wherein a diameter of the microcapsules is from 50 µm to 800 µm and the layered coating comprises:

(i) a first layer (B) surrounding the core comprising:
a colorant, and at least one binder selected from the group consisting of a polymer and a lipid-based material;
(ii) a second layer (C) surrounding the first layer (B), comprising: titanium dioxide particles, and at least one binder selected from the group consisting of a polymer and a lipid-based material;
(iii) optionally a third layer (D) surrounding the second layer (C) comprising:
a colorant, and at least one binder selected from the group consisting of a polymer and a lipid-based material;
(iv) optionally a fourth layer (E) surrounding the third layer (D), if present, or surrounding the second layer (C), comprising a wall-forming polymer.

9. The changing color composition according to claim 1, wherein the weight of the microcapsules is from 0.1% to 20% by weight based on the weight of the composition.

10. The changing color composition according to claim 1, which is in the form of a water-in-oil emulsion or an oil-in-water emulsion.

11. The changing color composition according to claim 1, wherein the amount of water is at least 30% by weight relative to the total weight of the composition.

12. The changing color composition according to claim 1, wherein at least one layer of the microcapsules is obtained by a fluid bed process.

13. A cosmetic process for caring for and/or making up a keratinic material, comprising contacting the changing color composition according to claim 1 with the keratinic material.

* * * * *

UNITED STATES PATENT AND TRADEMARK OFFICE
CERTIFICATE OF CORRECTION

PATENT NO. : 9,662,283 B2  
APPLICATION NO. : 14/372862  
DATED : May 30, 2017  
INVENTOR(S) : Cyril Lemoine et al.

Page 1 of 1

It is certified that error appears in the above-identified patent and that said Letters Patent is hereby corrected as shown below:

On the Title Page

Column 1, Line 22 Item (30) Foreign Application Priority Data:  
Change "(WO)" to --(CN)--

Signed and Sealed this  
Nineteenth Day of June, 2018

Andrei Iancu  
*Director of the United States Patent and Trademark Office*